(12) United States Patent
Wisniewski et al.

(10) Patent No.: US 6,313,091 B1
(45) Date of Patent: Nov. 6, 2001

(54) PHARMACEUTICAL COMPOSITIONS CONTAINING TSG-6 FOR TREATING INFLAMMATORY DISEASES AND CANCER-RELATED PATHOLOGIES AND METHOD

(75) Inventors: Hans-Georg Wisniewski; Jan Vilcek; Bruce Cronstein, all of New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/000,179
(22) PCT Filed: Jul. 19, 1996
(86) PCT No.: PCT/US96/11995
  § 371 Date: May 5, 1998
  § 102(e) Date: May 5, 1998
(87) PCT Pub. No.: WO97/04075
  PCT Pub. Date: Feb. 6, 1997

Related U.S. Application Data

(60) Provisional application No. 60/001,311, filed on Jul. 20, 1995.

(51) Int. Cl.[7] .......................... A61K 38/00; C07K 14/00; C07H 21/02; A01N 37/18; C12P 21/06
(52) U.S. Cl. .......................... 514/12; 530/350; 530/351; 530/395; 514/2; 536/23.1; 435/69.1; 435/252.3; 435/320.1
(58) Field of Search .......................... 435/69.1, 252.3, 435/320.1; 536/23.1; 514/44, 2, 12; 530/350, 351, 395

(56) References Cited

U.S. PATENT DOCUMENTS

| | | | |
|---|---|---|---|
| 5,386,013 | * | 1/1995 | Lee et al. .......................... 530/350 |
| 5,846,763 | * | 12/1998 | Lee et al. .......................... 435/69.1 |

FOREIGN PATENT DOCUMENTS

WO 92/18160 * 10/1992 (WO) .......................... A61K/37/64

OTHER PUBLICATIONS

Orkin et al "Report and Recommendations of the Panel to Assess the NIH Investment in Research on Gene Therapy", Dec. 1995.*

Ledley et al. Pharmaceutical Research. 13: 1595–1613, Nov. 1996.*

(List continued on next page.)

*Primary Examiner*—Karen Cochrane Carlson
*Assistant Examiner*—Rita Mitra
(74) *Attorney, Agent, or Firm*—Browdy and Neimark

(57) ABSTRACT

Pleiotropic pro-inflammatory cytokines, such as TNF and IL-1, induce expression of a protein molecule, termed TSG-6, in connective tissue cells. TSG-6, or pharmaceutical compositions containing TSG-6, can be used to treat inflammatory diseases and disorders and cancer-related pathologies. Inflammatory diseases and disorders, or cancer related pathologies, can also be treated by introducing human cells transfected with a DNA molecule containing a DNA segment encoding TSG-6 protein, into humans to express therapeutically effective amounts of TSG-6 in vivo or by introducing a vector carrying a DNA segment encoding TSG-6 protein directly into humans in vivo.

1 Claim, 11 Drawing Sheets

OTHER PUBLICATIONS

Verma et al. Nature. 389: 239–242, Sep. 1997.*
Wisniewski et al. Biochemistry. 33: 7423–7429, Jun. 1994.*
Miller et al. FASEB J. 9: 190–199, Feb. 1995.*
Takakura et al. Pharmaceutical Research. 13(6): 820–31, Jun. 1996.*
Klampfer, Lidija et al., "NF–IL6 and AP–1 cooperatively modulate the activation of the TSG–6 gene by tumor necrosis factor alpha and interleukin–1". Molecular and Cellular Biology, vol. 14, No. 10, pp. 6561–6569.
Journal of Immunology, vol. 150 (08 Part 02), issued May 21–25, 1993, "TSG–6: A cytokine and LPS–inducible secreted 35 KDA glycoprotein associated with arthritis and inflammation." abs. 127 A.
Journal of Cellular Biochemistry, (18 Part A), issued Jan. 16–23, 1994, Wisniewski et al., "TSG–6, An arthritis–associated hyaluronan binding protein, forms a stable complex with inter–alpha–inhibitor VIA a glycosaminoglycan crosslink", pp. 338, abs. #EZ508.

* cited by examiner

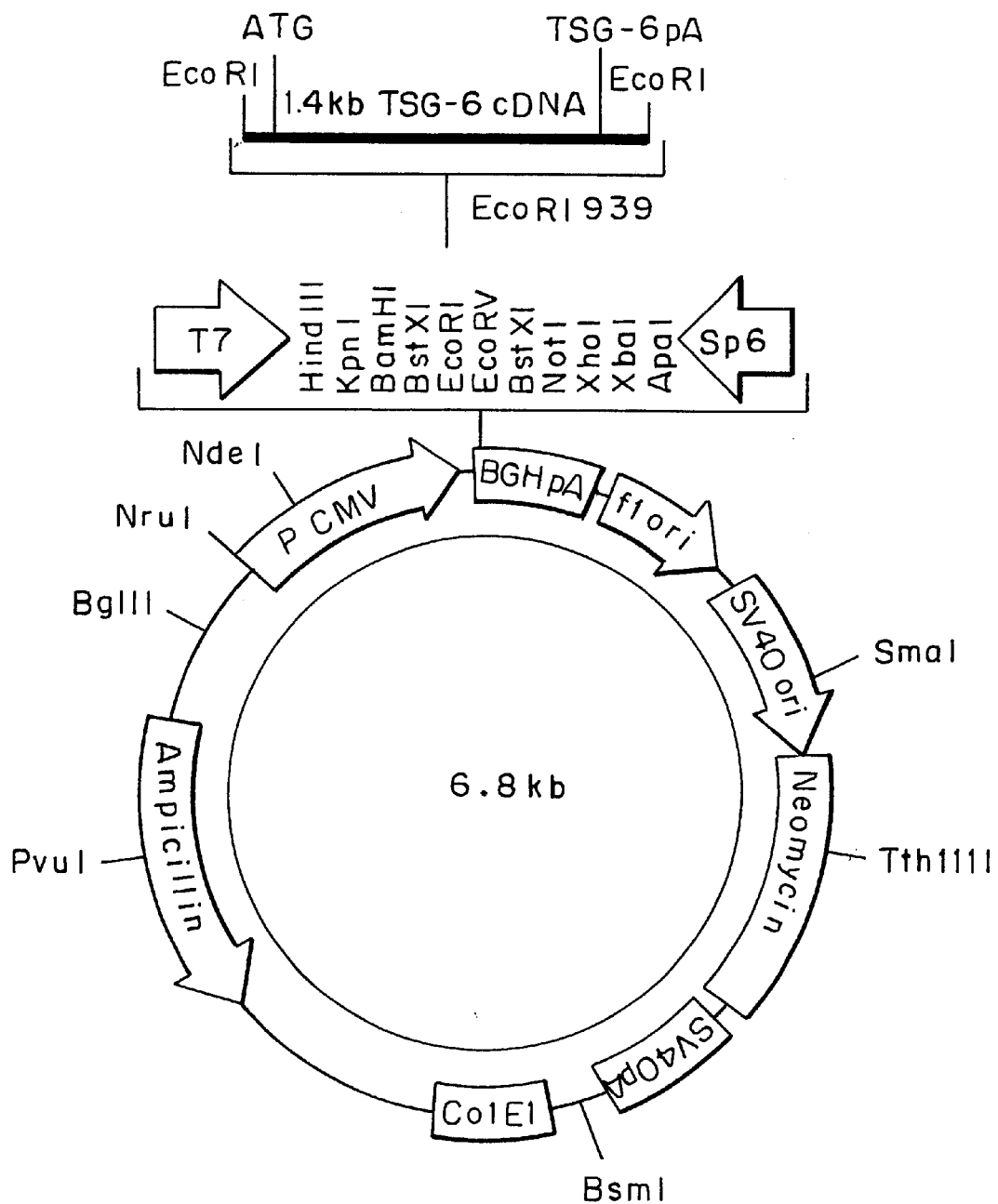

PHARMACEUTICAL COMPOSITIONS CONTAINING TSG-6 FOR TREATING INFLAMMATORY DISEASES AND CANCER-RELATED PATHOLOGIES AND METHOD

This application is a 371 of PCT/US96/11995 filed on Jul. 19, 1996, which claims benefit of U.S. Pat. No. 60/001,311 filed on Jul. 20, 1995.

BACKGROUND OF THE INVENTION

1. Field of the Invention

The invention relates to pharmaceutical compositions containing TSG-6 protein, inducible in connective tissue cells by tumor necrosis factor or interleukin-1, and methods for treating inflammatory diseases and disorders, or cancer-related pathologies.

2. Description of the Background Art

Tumor necrosis factor (TNF) is a powerful pleiotropic cytokine important in host defenses against tumors and infectious agents. TNF has also been implicated in the pathology of some neoplastic diseases, infections and autoimmune disorders as well as in various pro-inflammatory actions which result in tissue injury. TNF is an extremely "versatile" and clinically significant cytokine. Most of its actions are likely to be mediated by the activation or inactivation of specific genes in the cells upon which it acts. One exception to this mode of action is the rapid cytotoxic effect of TNF on certain target cells; this effect is augmented by inhibitors of RNA or protein synthesis and does not appear to depend on the modulation of gene expression (Matthews, N., *Br. J. Cancer* 48:405 (1983)). Many specific gene products have been shown to be up-regulated in TNF-treated cells.

A TNF-stimulated gene, abbreviated as TSG-6 gene, was originally isolated from a cDNA library prepared from TNF-treated normal human fibroblasts (Lee et al., *Mol. Cell. Biol.* 10:1982–1988, 1990). Early studies showed that TSG-6 gene transcription was induced by the pro-inflammatory cytokines TNF and IL-1 (Lee et al., *J. Cell Biol.* 116:545–547, 1992) or by bacterial LPS (Wisniewski et al., *J. Immunol.* 151:6593–6601, 1993) in fibroblasts, mononuclear cells, chondrocytes and synovial cells. TSG-6 codes for a secretory 35-kDa glycoprotein, designated TSG-6 protein, that is a member of the hyaladherin family of hyaluronan binding proteins (Lee et al., supra, 1992; Toole, In *Cell Biology of Extracellular Matrix*, Hay (ed.), 2nd ed., Plenum Press, New York, p. 305–341, 1991). Sequencing of the cDNA revealed an open reading frame coding for a polypeptide of 277 amino acids including a cleavable signal peptide (Lee et al., supra, 1992). In its N-terminal half, the predicted amino acid sequence shows 36–40% homology to members of the hyaladherin family of proteins that includes the lymphocyte homing/hyaluronan receptor CD44, cartilage link protein, and the proteoglycan core proteins aggrecan and versican (Lee et al., supra, 1992). The C-terminal half of TSG-6 shares 30% sequence homology with the A chain of complement Clr. This homology region forms a so-called CUB domain which is a motif found in proteins that are developmentally regulated (Bork et al., *J. Mol. Biol.*, 231:539–545, 1993). The rabbit homologue of TSG-6 was recently cloned and shown to be a developmentally regulated protein exhibiting 94% identity to human TSG-6 at the amino acid level (Feng et al., *J. Biol. Chem.*, 268:9387–9392, 1993).

Two N-glycosylation consensus sequences are present in TSG-6, and the presence of N-linked carbohydrate was experimentally confirmed (Lee et al., supra, 1992). Like other hyaladherins, TSG-6 protein binds specifically to hyaluronan. TSG-6 expression is tightly regulated, with its transcription in fibroblasts rapidly activated by stimulation with the pro-inflammatory cytokines IL-1 or TNF-α (Lee et al., supra, 1990; *J. Biol. Chem.* 268:6154–6160, 1993). High levels of TSG-6 protein were found in synovial fluids of patients with rheumatoid arthritis and some other forms of arthritis, whereas no TSG-6 protein was detected in synovial fluids from normal human joints (Wisniewski et al., supra, 1993). In addition, synoviocytes from the joints of rheumatoid arthritis patients showed constitutive TSG-6 expression that was further upregulated by IL-1 and TNF, cytokines that are regularly found in the rheumatoid synovial fluid or tissue (Wisniewski et al., supra, 1993).

TSG-6 binds firmly and selectively to a discrete protein present in animal sera (Wisniewski et al., In *Physiology and Pathophysiology of Cytokines*, Mantovani et al. (eds.), Biomedical Press, Augusta, Ga., p. 149–155, 1992; supra, 1993; *Biochemistry* 33:7423–7429, 1994). The complex of TSG-6 with its binding protein shows a molecular size of ~120 kDa on SDS-PAGE; the presence of this complex was also demonstrated in synovial fluids of arthritis patients (Wisniewski et al., supra, 1993). The TSG-6 binding protein was purified from human serum and shown by microsequencing to be identical to inter-α-inhibitor (IαI) (Wisniewski et al., supra, 1994).

Inter-α-inhibitor (IαI) is a member of a family of closely related proteins with serine proteinase inhibitory activity (Gebhard et al., *Biol. Chem. Hoppe-Seyler*, 371: Suppl. 13–22, 1990; Pratt et al., *Biochemistry* 26:2855–2863, 1987), consisting of IαI, pre-α-inhibitor (PαI), and inter-α-like inhibitor (IαLI) (Enghild et al., *J. Biol. Chem.* 264:15975–15981, 1989; Gebhard et al., supra, 1990; Rouet et al., *Biol. Chem. Hoppe-Seyler* 373:1019–1024, 1992). The protease inhibitory activity of these proteins resides exclusively in a polypeptide chain termed bikunin (Gebhard et al., *Eur. J. Biochem.* 181:571–576, 1989; Gebhard et al., supra, 1990) that is shared by all members of this family. The different proteins are formed by the linkage of bikunin to one or two of three heavy chains (HC1, HC2, HC3) which show 38–54% amino acid sequence homology to each other (Bourguignon et al., *Eur. J. Biochem.* 212:771–776, 1993). IαI consists of bikunin linked to both HC1 and HC2, PαI consists of bikunin linked to HC3, and IαI is a complex of bikunin with HC2 (Enghild et al., supra, 1989; Gebhard et al., supra, 1990; Rouet et al., supra, 1992). A chondroitin 4-sulfate chain whose reducing end is linked to $Ser^{10}$ of bikunin (Enghild et al., *J. Biol. Chem.* 266:747–751, 1991; Chirat et al., *Int. J. Biochem.* 23:1201–1203, 1991) cross-links the polypeptide chains of these complex protein molecules, which are all stable in SDS-PAGE under reducing conditions.

The bikunin chain is solely responsible for the protease inhibitory activity of IαI and of other members of this family. The protease inhibitory activity of IαI is specific for trypsin, chymotrypsin, plasmin, cathepsin G, acrosin, and leukocyte elastase (Steinbuch, *Meth. Enzymol.* 45:760–762, 1976; Jochum et al., *Hoppe Seylers Zeitschrift fur Physiologische Chemie* 364:1709–1715, 1983; Balduyck et al., *Biol. Chem. Hoppe-Seyler* 366:9–14, 1985; Bromke et al., *Biochem. Med.* 27:56–57, 1982, Lambin et al., *Thrombosis Res.* 13:563–568, 1978).

Although the trypsin-inhibitory activity of IαI has been known for a long time (Heide et al., *Clin. Chem. Acta* 11:82–85 (1965)), little is known about the functions of the different members of the IαI family. However, disease-associated presence in various tissues and fluctuations seen in the serum levels of IαI and IαI-related proteins suggest an involvement in pathologic processes. Daveau et al., *Biochem. J.* 292:485–4924 (1993) reported a distinct pattern of changes in serum concentrations of the different members of the IαI family during acute inflammation. Proteins identical with, or closely related to, the bikunin chain of IαI have been detected in stroma and the surrounding connective tissue of malignant tumors (Yoshida et al., *Cancer* 64:860–869 (1989)), in brain tissue of patients with Alzheimer's disease (Yoshida et al., *Biochem. Biophys. Res. Commun.* 174:1015–1021 (1991)), and in serum and urine of patients with inflammatory disease, cancer, and leukemias (Rudman et al., *Cancer Res.* 36:1837–1846 (1976); Franck et al., *Scand. J. Clin. Lab. Invest.* 43:151–155 (1976); Chawla et al.,*J. Cell Biochem.* 42:207–217 (1990)). A link between IαI and rheumatoid arthritis was suggested over 20 years ago when Becker et al., *Arthritis Rheum.* (1971), found IαI associated with hyaluronan in the synovial fluid of patients with rheumatoid arthritis, whereas no IαI was detectable in control synovial fluids. This finding was confirmed and extended to show that IαI associates in vitro with hyaluronan isolated from the synovial fluid of healthy subjects (Hutadilok et al., *Ann. Rheum. Dis.* 47:377–385 (1988)). Huang et al., *J. Biol. Chem.* 268:26725–26730 (1993) showed recently that in the presence of serum the two heavy chains of IαI become covalently associated with hyaluronan.

In view of the inducibility of TSG-6 by the proinflammatory cytokines TNF and IL-1, as well as by LPS, it appeared likely that TSG-6 would play a role in inflammation. This view was reinforced by the demonstration that TSG-6 protein is present in the synovial fluids (and, at lower concentrations, also in the sera) of patients with rheumatoid arthritis and some other forms of arthritis (Wisniewski et al., supra, 1993). TNF, IL-1, and LPS are known to stimulate the synthesis of many other proinflammatory secreted proteins, including other cytokines, such as IL-8 (Matsushima et al., *J. Exp. Med.* 167:1883–1893, 1988), and the metalloproteinases collagenase and stromelysin (Brenner et al., *Nature* 337:661–663, 1989; Dayer et al., *J. Exp. Med.* 162:2163–2168, 1985; Quinones et al., *J. Biol. Chem.* 264:8339–8344, 1989). Therefore, the initial expectation was that TSG-6 protein would also turn out to have a pro-inflammatory function and that methods of treating inflammatory conditions would involve inhibiting the proinflammatory effect of TSG-6.

U.S. Pat. No. 5,386,013 discloses that the TSG-6 protein, encoded by a TNF-stimulated gene, is expected to have a pro-inflammatory effect as antibodies specific for TSG-6 protein would be used in a method of treating inflammatory conditions by binding to TSG-6 and inhibiting its activity.

Citation of any document herein is not intended as an admission tha t such document is pertinent prior art, or considered material to the patentability of any claim of the present application. Any statement as to content or a date of any document is based on the information available to applicant at the time of filing and does not constitute an admission as to the correctness of such a statement

SUMMARY OF THE INVENTION

It has now been unexpectedly discovered that TSG-6 produces an anti-inflammatory effect in vivo. The expectation from previous studies was that TSG-6 functions in a pro-inflammatory fashion, and it is totally surprising that it has the opposite effect of producing a potent anti-inflammatory effect. It has also beeen discovered that TSG-6 forms a complex with IαI and potentiates the anti-plasmin activity of IαI.

Specifically, the present invention provides a pharmaceutical composition for treating inflammatory diseases and disorders, or cancer-related pathologies, containing TSG-6 and a pharmaceutically acceptable carrier, wherein the full length unglycosylated protein molecule a molecular weight of about 28 kDa and has the amino acid sequence SEQ ID NO:2. In a glycosylated form, the glycoprotein may have molecular weights in the range of about 32 kDa to 43 kDa.

A further pharmaceutical composition for treating inflammatory diseases and disorders, or cancer-related pathologies contains a complex of TSG-6 and IαI.

The present invention is further directed to a method for treating inflammatory diseases and disorders in humans and a method for inhibiting tumor metastases, invasive tumor growth or cancer-related pathologies in humans by administering TSG-6.

The present invention is further directed to another method for treating inflammatory diseases and disorders, or cancer-related pathologies, by introducing human cells, transfected with a DNA molecule containing a DNA segment encoding TSG-6, into humans to express therapeutically effective amounts of TSG-6 in vivo or by introducing a vector carrying a DNA segment encoding TSG-6 directly in humans in vivo.

BRIEF DESCRIPTION OF THE DRAWINGS

FIG. 12 shows a schematic diagram of PcDNA3/TSG-6, a mammalian expression vector for recombinant TSG-6 protein.

DETAILED DESCRIPTION OF PREFERRED EMBODIMENTS

Figure 1:
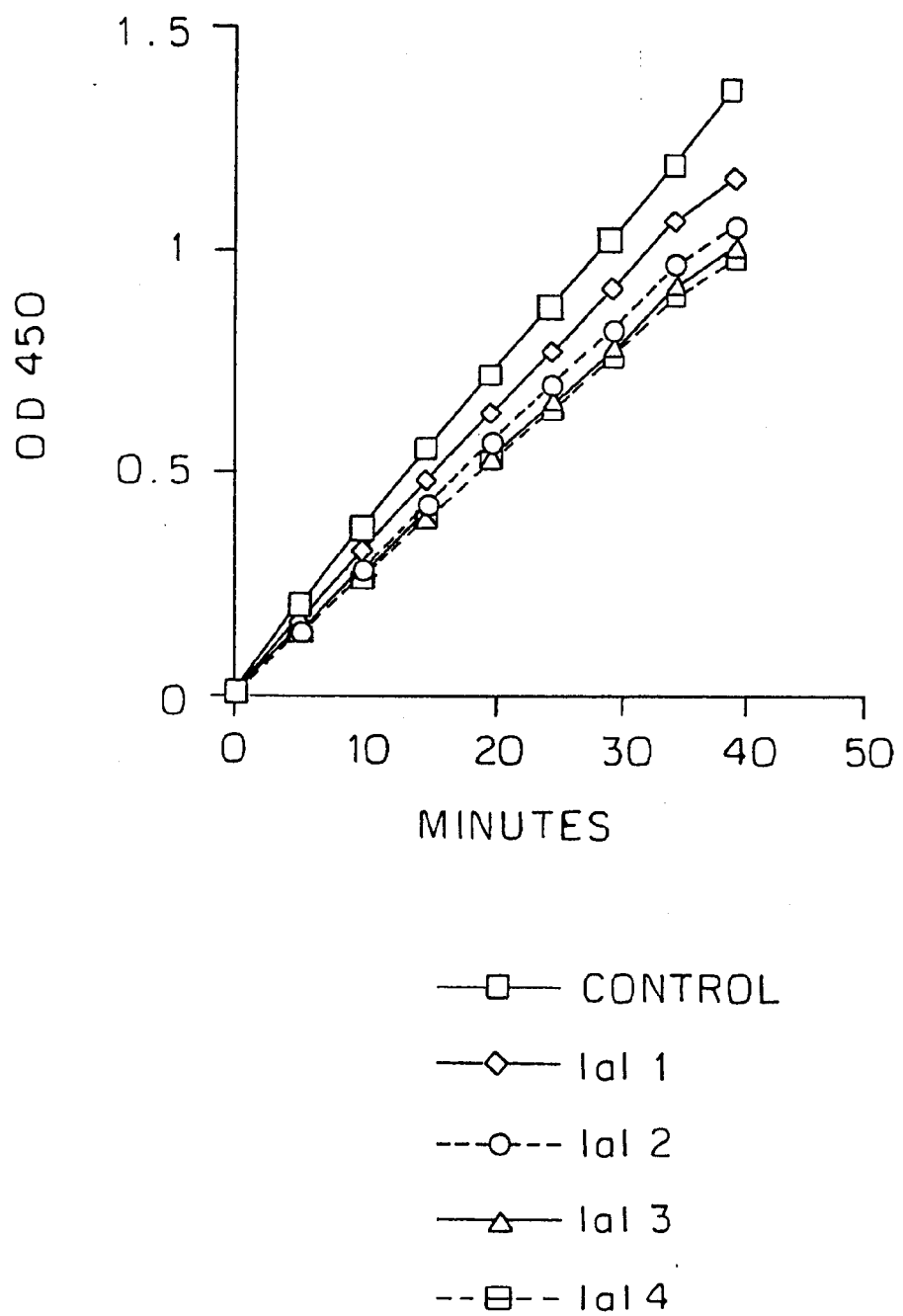
FIG. 1 shows the inhibition of plasmin by different concentrations of inter-α-inhibitor (IαI). The protease activity of plasmin was assayed as described in Example II where Chromozym$_R$ PL was used as a substrate with 3.4 nM plasmin in the absence of inhibitor (control) or in the presence of 18 nM (1), 36 nM (2), 54 nM (3), 72 nM (4) IαI.

A number of genes activated in human FS-4 fibroblasts by tumor necrosis factor (TNF) have been termed "TNF-stimulated genes" (abbreviated TSG). It should be appreciated that such genes, and the proteins and glycoproteins they encode, are induced by cytokines more generally, including TNF, IL-1, and, in some cases, interferons. One of the TSG genes has been designated TSG-6 (see Lee et al., U.S. Pat. No. 5,386,013). TSG-6 is useful for treating diseases and conditions in which the activity of such cytokines is associated with the pathophysiology. Such diseases include chronic inflammation, such as rheumatoid arthritis, and cancer.

Inflammatory conditions treatable with TSG-6 can also include, but is not limited to, the following, which can include TNF related pathologies:

(A) acute and chronic immune and autoimmune pathologies, such as systemic lupus erythematosus (SLE), rheumatoid arthritis, thyroidosis, graft versus host disease, scleroderma, diabetes mellitus, Graves' disease, and the like;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as HIV, AIDS (including symptoms of cachexia, autoimmune disorders, AIDS dementia complex and infections);

(C) inflammatory diseases, such as various forms of arthritis, chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology;

(D) neurodegenerative diseases, including, but are not limited to
demyelinating diseases, such as multiple sclerosis and acute transverse myelitis;
extrapyramidal and cerebellar disorders such as lesions of the corticospinal system;
disorders of the basal ganglia or cerebellar disorders;
hyperkinetic movement disorders such as Huntington's Chorea and senile chorea;
drug-induced movement disorders, such as those induced by drugs which block CNS dopamine receptors;
hypokinetic movement disorders, such as Parkinson's disease;
Progressive supranucleo palsy;
Cerebellar and Spinocerebellar Disorders, such as astructural lesions of the cerebellum;
spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi-system disorder);
demyelinating core disorders, such as multiple sclerosis, acute transverse myelitis;
disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Sub-acute sclerosing panencephalitis, Hallerrorden-Spatz disease; and Dementia pugilistica, or any subset thereof;

(E) malignant pathologies or other malignancies, such as, but not limited to carcinomas, sarcomas, leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); and (F) alcohol-induced hepatitis.

See, e.g., Berkow et al, eds., *The Merck Manual*, 16th edition, chapter 11, pp 1380–1529, Merck and Co., Rahway, N.J., 1992, which reference, and references cited therein, are entirely incorporated herein by reference.

In the context of the present invention, the term "TNF-stimulated gene 6 protein" or "TSG-6" are intended to encompass any isolated, purified TSG-6 protein from natural sources, such as human serum, or derived from expression systems for recombinant TSG-6, or chemically synthesized. Human TSG-6 has the sequence of SEQ ID NO:1. The term is also intended to include polypeptides or proteins substantially corresponding to TSG-6, having TSG-6 biological activity. Also included within the scope of this term are salts and functional derivatives of any such polypeptides or protein.

A polypeptide or protein "substantially corresponding" to TSG-6 includes not only TSG-6 but also polypeptides or proteins that are "muteins" of TSG-6, as well as active fractions of TSG-6 or its muteins.

"Muteins" that substantially correspond to TSG-6 are those proteins in which one or more amino acid of the TSG-6 amino acid sequence have been replaced with another amino acid and/or deleted, provided that the resulting protein exhibits substantially the same biological activity as TSG-6 and is pharmaceutically acceptable. The "biological activity" of TSG-6 as used herein is specifically meant to include the anti-inflammatory or protease-inhibitory (e.g., plasmin-inhibitory) activity thereof.

In order to substantially correspond to TSG-6, the changes in the sequence of SEQ ID NO:1 must be relatively minor. Preferably, there are no more than ten changes in the 277 amino acid sequence, more preferably no more than five, and most preferably no more than three such changes. While any technique can be used to find potentially biologically active proteins which substantially correspond to TSG-6, one such technique is the use of conventional mutagenesis techniques on the DNA encoding the protein, resulting in a few modifications. The proteins expressed by such clones can then be screened for anti-inflammatory or protease-inhibitory activity.

Rather than random changes, it is preferred to screen only those changes which would not be expected to change the activity of the protein. Thus, "conservative" changes are the first to be screened as these would not be expected to substantially change the size, charge or configuration of the protein and thus would not be expected to change the biological properties thereof.

Conservative substitutions of TSG-6 include a mutein wherein at least one amino acid residue in the polypeptide has been conservatively replaced by a different amino acid. Such substitutions preferably are made in accordance with the following list as presented in Table IA which substitutions may be determined by routine experimentation to provide modified structural and functional properties of a synthesized polypeptide molecule, while maintaining or mimicking biological activity characteristic of TSG-6.

TABLE IA

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of TSG-6 are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1–2 of Schulz et al., supra and FIGS. 3–9 of Creighton, supra. Based on such an analysis, alternative conservative substitutions are defined herein as exchanges within one of the following five groups:

TABLE IB

| | |
| --- | --- |
| 1. | Small aliphatic, nonpolar or slightly polar residues: Ala, Ser, Thr (Pro, Gly); |
| 2. | Polar negatively charged residues and their amides: Asp, Asn, Glu, Gln; |
| 3. | Polar, positively charged residues: His, Arg, Lys; |
| 4. | Large aliphatic nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This however tends to promote the formation of secondary structure other than $\alpha$-helical. Pro, because of its unusual geometry, tightly constrains the chain and generally tends to promote $\beta$-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. $\alpha$-helix or $\beta$-sheet, as well as changes in physiological activity, e.g. anti-inflammatory assay, plasmin assays.

Examples of production of amino acid substitutions in proteins which can be used for obtaining muteins of TSG-6 for use in the present invention include any known method steps, such as presented in U.S. Pat. Nos. 33,653, 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

One way to determine which portions of the molecule would be most likely to permit such changes without affecting the anti-inflammatory activity is to first test the effect of changes in various of the known domains of the TSG-6 protein. It has been shown in the examples herein that changes to amino acids in the hyaluronan binding domain can affect anti-inflammatory activity, so it would be expected that this domain was particularly sensitive to changes in the amino acid sequence. Changes to other domains, particularly in the C-terminal half of the protein, would be considered as higher priority for screening.

Another way to try to predict which residues may not be critical for biological activity is to sequence the corresponding protein from other species, particularly other mammalian species, and compare the sequences for areas of highest homology and areas of highest diversity. Changes in the non-conserved areas would be considered most ripe for conservative changes which do not affect the anti-inflammatory activity.

Cysteine residues are often considered prime candidates for substitution in order to enhance stability or to ease production and purification. It would not take undue experimentation to screen proteins with conservative changes of each of the cysteine residues for anti-inflammatory activity. It is known, for example, from U.S. Pat. No. 4,959,314 that serine often is substitutable for cysteine without affecting biological properties.

When the exact effect of the substitution or deletion is to be confirmed, one skilled in the art will appreciate that the effect of the substitution(s), deletion(s), etc. will be evaluated by routine screening assays, either immunoassays or bioassays to confirm biological activity, such as an anti-inflammatory activity or an anti-protease activity. For example, an anti-inflammatory bioassay using the murine air pouch model described in Example II can be used without undue experimentation to determine the presence or level of biological activity, i.e. anti-inflammatory activity, or an in vitro plasmin assay, also as described in Example II, can be used. Screening using such a standard test does not involve undue experimentation.

Additionally, muteins that substantially correspond to TSG-6 are those polypeptides or proteins where one or more amino acids, preferably no more than five, and more preferably no more than three amino acids, are inserted into the 277 amino acid sequence of TSG-6. Any such insertion within a domain of TSG-6 not expected to be particularly sensitive to changes in amino acid sequence can be also readily screened for TSG-6 anti-inflammatory biological activity in the same manner as described above for substitutions and deletions.

A substituted polypeptide typically is made by site-specific mutagenesis of the polypeptide molecule-encoding nucleic acid, expression of the mutant nucleic acid in recombinant cell culture, and, optionally, purification from the cell culture, for example, by the purification method for recombinant TSG-6 described in Example I.

The term "active fractions" of TSG-6 protein or mutein is intended to cover any fragment of the TSG-6 protein or mutein that retains TSG-6 anti-inflammatory biological activity (see Example II). For example, fragments can be readily generated from TSG-6 where successive residues can be removed from either or both the N-terminus or C-terminus of TSG-6, or from peptides obtained thereof by enzymatic or chemical cleavage of the polypeptide. Thus, multiple substitutions are not involved in screening for active fractions of TSG-6. If the removal of one or two amino acids from one end or the other does not affect the biological activity after testing in the standard tests, discussed above, such truncated polypeptides are considered to be within the scope of the present invention. Further truncations can then be carried out until it is found where the removal of another residue destroys the biological activity.

As used herein, the term "salts" refers to both salts of carboxyl groups and to acid addition salts of amino groups of the polypeptide molecule. Salts of a carboxyl group may be formed by means known in the art and include inorganic salts, for example, sodium, calcium, ammonium, ferric or zinc salts, and the like, and salts with organic bases as those formed, for example, with amine, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic aid or oxalic acid.

"Derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the pharmaceutical activity of the protein as described herein and do not confer toxic properties on compositions containing it. Derivatives may have chemical moieties such as carbohydrate or phosphate residues, provided such a fraction has the same anti-inflammatory biological activity as TSG-6 and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or 0-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

Such muteins, active fractions, derivatives or salts of TSG-6 are intended to be encompassed by the terms "TNF-stimulated gene 6 protein" or "TSG-6" as used herein.

Although TSG-6 is a protein or polypeptide, it is a sequence of amino acid residues. A polypeptide consisting of a larger sequence which includes the entire sequence of a TSG-6 protein or polypeptide, in accordance with the definitions herein, is intended to be included within the scope of a polypeptide "consisting essentially of" TSG-6 as long as the additions do not affect the basic and novel characteristics of the invention, i.e., if they either retain the biological activity of TSG-6 or can be cleaved to leave a protein or polypeptide having the biological activity of TSG-6. Similarly, a protein or polypeptide "comprising" TSG-6 is intended to include a protein or polypeptide of any length which includes the entire sequence of a TSG-6 protein or polypeptide as defined herein. Thus, for example, the present invention is intended to include fusion proteins of TSG-6 with other amino acids or peptides.

As discussed herein, TSG-6 may be further modified for purposes of drug design, such as, for example, to reduce immunogenicity, to promote solubility or enhance delivery, or to prevent clearance or degradation.

Accordingly, TSG-6 for use in the present invention, or nucleic acids encoding same, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, eds., *Current Protocols in Molecular Biology*, Wiley Intersciences, N.Y. (1987–1995) at §§A.1.1-A.1.24, and Sambrook et al, In: *Molecular Cloning: A Laboratory Manual*, second edition, Cold Spring Harbor Press, N.Y. (1989), at Appendices C and D.

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al.,

*Molecular Cell Biology*, Scientific American Books, Inc., publisher, New York, N.Y. (1986); Lewin, B. M., Genes II, John Wiley & Sons, publishers, New York, N.Y. (1985); Old, R. W., et al., *Principles of Gene Manipulation: An Introduction to Genetic Engineering*, 2nd edition, University of California Press, publisher, Berkeley, Calif. (1981); and Sambrook, J. et al., *Molecular Cloning: A Laboratory Manual*, Cold Spring Harbor Laboratory, Cold Spring Harbor, N.Y. (1989) and Ausubel et al., supra. These references are hereby incorporated by reference.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "vector" is meant a DNA molecule, derived from a plasmid, bacteriophage or viral DNA, into which fragments of DNA may be inserted or cloned. A vector will contain one or more unique restriction sites, and may be capable of autonomous replication in a defined host or vehicle organism such that the cloned sequence is reproducible.

An "expression vector" is a vector which (due to the presence of appropriate transcriptional and/or translational control sequences) is capable of expressing a DNA (or cDNA) molecule which has been cloned into the vector to thereby produce a polypeptide or protein. Expression of the cloned sequences occurs when the expression vector is introduced into an appropriate host cell.

A DNA sequence or segment encoding a TSG-6 protein may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook, J. et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary, but shall in general include regions such as those 5'-non-coding sequences involved with initiation of transcription and translation, such as the TATA box, capping sequence, CCAAT sequence, and the like.

If desired, the non-coding region 3' to the gene sequence coding for the protein may also be obtained. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA are operably linked if transcription commencing in the promoter sequence will produce an RNA transcript of the operably linked second sequence. In order to be "operably linked", it is not necessary that two sequences be immediately adjacent to one another.

A promoter is a double-stranded DNA molecule which is capable of binding RNA polymerase and promoting the transcription of an "operably linked" nucleic acid sequence. As used herein, a "promoter sequence" is the sequence of the promoter which is found on that strand of the DNA which is transcribed by the RNA polymerase.

Many possible vector systems are available for the expression of TSG-6. A wide variety of transcriptional and translational regulatory sequences may be employed, depending upon the nature of the host. The transcriptional and translational regulatory signals may be derived from viral sources, such as adenovirus, cytomegalovirus (CMV), bovine papilloma virus, Simian virus 40, retroviruses, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated.

One embodiment of the present invention is directed to a method for treating inflammatory diseases and disorders, or cancer-related pathologies by providing humans with the capability of producing a therapeutically effective amount of TSG-6 in vivo. A mammalian expression vector, such as pcDNA3, carrying a DNA segment encoding TSG-6 can be used to transfect human cells.

Transfected human cells can then be introduced into humans according to methods established by Anderson, U.S. Pat. No. 5,399,346, in order to confer the capability of expressing a therapeutically effective amount of TSG-6 to treat the inflammatory or cancer-related conditions.

Another possibility for introducing genes into humans for in vivo expression is encapsulation of a mammalian expression vector carrying the DNA segment encoding TSG-6 protein into a liposome using various lipid and solvent conditions, and injecting the liposome into animal tissues, as has been described and demonstrated (Ghirlando et al., *Biochemistry*, 31:7110–7119 (1992); Braulin et al., *Biopolymers*, 21:1301–1309 (1982); Zhu et al., *Science*, 261:209–211 (1993); Alino et al., *Research Communications*, 192:174–181 (1993); Takeshits et al., *Lab. Invest.*, 71:387–391 (1994); Jarnagin et al., *Nucleic Acids Res.*, 20:4205–4211 (1992); Philip et al., *J. Biol. Chem.*, 268:16087–16090 (1993).

Another technique for introducing genes into humans for in vivo expression is by means of facilitated DNA inoculation. Plasmid DNA that supports in vivo expression of TSG-6 can be administered intramuscularly in a human manner so as to express TSG-6. Uptake and expression are significantly enhanced if the DNA is administered in conjunction with a facilitating agent such as bupivacaine-HCl. See, for example, Coney et al, *Vaccine*, 12:1545–1550 (1994); Thomason et al, *Am. J. Physiol.* 258 (3 Part 1):C578–C582 (1990); Nabel et al, *Science*, 249:1285–1288 (1990); Wang et al, *Ann. N.Y. Acad. Sci.*, 772:186–197 (1995); and Tang et al, *Nature*, 356:152–154 (1992), the technique of gene inoculation disclosed in each of which being hereby incorporated herein by reference. Preferably, the DNA will be inoculated directly into the area in the patient where the inflammation or cancer-related pathology is located. An amount of DNA is inoculated sufficient to express an effective amount of TSG-6.

Many other methods can be used to introduce and express a vector carrying the DNA segment encoding TSG-6 in humans. Currently available vectors, such as adenovirus, etc. and techniques for use in human gene therapy are reviewed by Johnson, *Chest* 107(2 Suppl.):77S–83S (1995). A person skilled in the art can construct vectors carrying a DNA segment encoding TSG-6 and introduce them directly into a human in order to express a therapeutically effective amount of TSG-6 in vivo.

The target cells may belong to human tissues (including organs), including cells belonging to the connective tissue (e.g. joint tissues, synovial cells, chondrocytes), the nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin or the muscles. Alternatively, the cells may be cancer cells in humans or cancer cells derived from any human organ or tissue.

It is known that TSG-6 protein forms a stable complex with components of inter-α-inhibitor (IαI), a normal constituent of plasma. IαI is an inhibitor of serine proteases including trypsin, chymotrypsin, plasmin, leukocyte elastase and cathepsin G. The TSG-6/IαI complex consists of TSG-6 and two polypeptide chains from the IαI molecule: heavy chain 2 and bikunin. Bikunin is responsible for the protease-inhibitory activity of IαI. These three polypeptide components appear to be crosslinked through a chondroitin sulfate chain (Wisniewski et al., supra, 1994). The results presented in Example II show that TSG-6 and IαI synergize to inhibit the serine protease activity of plasmin. The role of plasmin and its activator, plasminogen activator, in tumor metastasis and invasiveness has been extensively documented (Moscatelli et al., *Biochem. Biophys. Acta*, 948:67–85, 1988; Opdenakker et al., *Cytokine*, 4:251–258, 1992; Stetler-Stevenson et al., *Ann. Rev. Cell Biol.* 9:541, 1993). Based on our demonstration that the interaction of TSG-6 and IαI leads to a cooperative inhibition of plasmin activity, it can be predicted that TSG-6 will interfere with tumor metastasis and invasive tumor cell growth by inhibiting the activation of the protease network which is under the control of plasmin. Therefore, TSG-6 protein can be expected to inhibit tumor metastases and the invasive growth of malignant tumors. According to the present invention, cancer-related pathologies, such as tumor metastases and the invasive growth of tumors, may be treated by administering TSG-6 as described above.

A link between TSG-6 and inflammation was first established by our demonstration that high concentrations of TSG-6 are present in the synovial fluid of patients with rheumatoid arthritis and some other forms of arthritis, whereas no TSG-6 was detectable in control synovial fluids (Wisniewski et al., supra, 1993). Synovial cells from a rheumatoid arthritis patient showed high levels of constitutive TSG-6 production, and both synovial cells and chondrocytes in culture showed increased TSG-6 production in response to IL-1 or TNF-α (Wisniewski et al., supra, 1993).

The degradation of cartilage associated with rheumatoid arthritis, osteoarthritis, and other inflammatory joint diseases is the result of the activity of matrix metalloproteinase (MMPs) such as collagenases, gelatinases, and stromelysins which are produced by a variety of cells after stimulation with the proinflammatory cytokines IL-1 or TNF-α. These enzymes, however, have to be activated from inactive zymogen forms by a proteolytic cleavage. This activation is a function of the serine protease plasmin and is under the control of the plasmin/plasminogen activator system (Alexander et al., In *Cell Biology Extracellular Matrix*, 2nd ed., Hay (ed.), Plenum Press, New York, p. 255–302, 1991). The role of plasmin in arthritis and other inflammatory processes is threefold: (1) plasmin acts as an effector protease cleaving a limited range of matrix proteins, (2) plasmin proteolytically activates MMPs, the proteases responsible for most of the proteolytic damage observed in arthritis, and (3) plasmin facilitates its own activation through a positive feedback loop including another serine protease, urokinase type plasminogen activator (Gonias, *Exp. Hematol.* 20:301–311, 1992; Moscatelli et al., supra, 1988; Opdenakker et al., supra, 1992). TSG-6 and IαI was shown to potently synergize to inhibit the serine protease plasmin (See Example II), suggesting that TSG-6 may interfere with the plasmin-mediated activation of MMPs.

Therefore, according to the present invention, inflammatory diseases, disorders or pathologies, such as, for example, rheumatoid arthritis and other inflammatory connective tissue disorders, may be treated by administering TSG-6.

Also intended for treating inflammatory diseases and disorders, or cancer-related pathologies, is a pharmaceutical composition containing a complex of TSG-6 protein and IαI, or components of IαI, to potentiate the plasmin-inhibitory activity of IαI.

As used herein, the term "prevention" of a condition, such as an inflammatory response, infectious disease or a malignant tumor, in a subject involves administration of TSG-6 prior to the clinical onset of the disease. "Treatment" involves administration of the protective composition after the clinical onset of the disease. For example, successful administration of TSG-6, after development of an inflammatory condition, a malignant tumor or an infection comprises "treatment" of the disease. While the invention is particularly useful in the treatment of humans, it is intended for veterinary uses as well.

The active principle of the present invention may be administered by any means that achieve its intended purpose, e.g., to treat rheumatoid arthritis or other inflammatory conditions, malignant tumors, infections, and the like.

For example, administration may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A typical regimen for preventing, suppressing, or treating a condition such as chronic inflammation, as in rheumatoid arthritis, or a malignant tumor, comprises administration of a therapeutically effective amount of the TSG-6 administered over a period of one or several days, up to and including between one week and about six months.

It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art.

The total dose required for each treatment may be administered by multiple doses or in a single dose. The protein, fragment thereof or functional derivative may be administered alone or in conjunction with other therapeutics directed to the condition, or directed to other symptoms of the condition.

Therapeutically effective amounts of TSG-6 are from about 0.01 μg to about 100 mg/kg body weight, preferably from about 10 μg to about 50 mg/kg body weight, and more preferably from about 2 μg to about 1 mg/kg body weight and any range therein.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising the TSG-6 include all compositions wherein TSG-6 is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically.

Suitable formulations for parenteral administration include aqueous solutions of the active compounds in water-soluble form, for example, water-soluble salts. In addition, suspension of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Pharmaceutical compositions include suitable solutions for administration by injection or orally, and contain from about 0.01 to 99 percent, preferably from about 20 to 75 percent of active component (i.e., TSG-6) together with the excipient. Pharmaceutical compositions for oral administration include tablets and capsules. Compositions which can be administered rectally include suppositories.

U.S. Pat. No. 5,386,013 relating to TSG-6 protein, functional derivatives thereof, DNA coding therefor, expression vehicles, host cells transformed or transfected with the DNA molecule, methods for producing the protein and DNA, antibodies specific for TSG-6 protein, methods disclosed therein, etc., is hereby entirely incorporated by reference. Also incorporated herein be reference is copending application Ser. No. 08/242,097 filed May 13, 1994, which is a continuation-in-part of the application that issued as said U.S. Pat. No. 5,386,013.

Having now generally described the invention, the same will be more readily understood through reference to the following examples which are provided by way of illustration, and are not intended to be limiting of the present invention, unless specified.

EXAMPLE I

Experimental Procedures

Materials.

Chondroitin sulfate ABC lyase from Proteus vulgaris (EC 4.2.2.4) and hyaluronate lyase from Streptomyces hyalurolyticus (EC 4.2.2.1) were purchased from Sigma, rabbit anti-human inter-α-inhibitor (IαI) immunoglobulin was from Dako (Glostrup, Denmark) and [$^{35}$S]methionine/[$^{35}$S]cysteine (Trans $^{35}$S-label) was purchased from ICN. Immunoprecipitin (heat-killed, formalin fixed *Staphylococcus aureas*, SAC) was from GIBCO BRL, and EX-CELL 300 and EX-CELL 400 medium was from JRH Biosciences (Lenexa, Kans.). Albumin Removal AFFINI-FILTERS were from Affinity Technology, New Brunswick, N.J., Centricon-10 concentrators were from Amicon, and polyvinylidene difluoride (PVDF) membranes (Immobilon-P) were from Millipore. FPLC equipment and separation matrices were from Pharmacia. All other chemicals were purchased from commercial suppliers and were of analytical or molecular biology grade.

Production and Purification of Recombinant Human TSG-6 Protein.

Recombinant *Autographa californica* nuclear polyhedrosis virus (genus Baculovirus) containing human TSG-6 cDNA (Wisniewski et al., *Physiology and Pathophysiology of Cytokines* (1992)) was used for the infection of High Five (TN-5B) insect cells from *Trichoplusia ni* (BTI-TN-5B1-4; Invitrogen, San Diego, Calif.). For high-level expression and purification of TSG-6 protein, TN-5B insect cells were grown in serum-free EX-CELL 400 medium. The cell culture medium was replaced 24 hrs. after inoculation of ~70–80% confluent cultures with recombinant virus and collected again 48 hrs. later. For purification of TSG-6 protein, cleared culture supernatant was directly loaded on a MonoS (HR5/5) column equilibrated with 20 mM 4-morpholineethanesulfonic acid (MES), pH 6.5. Bound protein was eluted with a linear gradient (20 mL) from 0 to 1 M NaCl in 20 mM MES, pH 6.5. Fractions containing the bulk of TSG-6 protein (0.45–0.65 M NaCl) were pooled, concentrated in Centricon-10 units, and applied onto a Superdex 75 (HR 10/30) column equilibrated with 20 mM MES, pH 6.5, 0.5 M NaCl. This resulted in the recovery of ≧95% pure TSG-6 protein as judged by silver staining of SDS-PAGE gels. About 1 μg of pure protein was recovered per 1 mL of culture supernatant. Microsequencing of the purified TSG-6 protein established Trp$^{18}$ as the N-terminus of the mature secreted glycoprotein (Table 2), which is in good agreement with the predicted cleavage site of the signal peptide sequence (Von Heijne, *J. Mol. Biol.* 173:243–251 (1984); *J. Mol.Biol.* 184:99–105 (1985).

Analysis of TSG-6 Binding to Carrier Protein.

To determine the presence of TSG-6 binding protein, samples to be analyzed were mixed with an equal volume of TSG-6-containing serum-free supernatants of TN-5B insect cells infected with recombinant Baculovirus and incubated at 37° C. for 30–60 min. (Purified TSG-6 protein was used in some experiments, as indicated.) Thereafter, the mixtures were analyzed for the presence of the 120-kDa complex by Western blotting with purified rabbit antibody to TSG-6 as described earlier (Wisniewski et al., supra, 1993). For detection of inter-α-inhibitor (IαI) epitopes by Western blotting, membranes were incubated with a rabbit anti-human IαI antibody (Dako) at a 1:2000 dilution for 1 hr.

Immunoprecipitation.

Human HepG2 hepatoma cells producing IαI constitutively (Bourguignon et al., *Biochem. J.* 261:305–308 (1989)) were grown in serum-free EX-CELL 300 medium. [$^{35}$S]Methionine(Tran$^{35}$S-label) was added to about 75% confluent HepG2 cell cultures in a 25 cm$^2$ flask (500 μCi/culture), and the culture supernatant was collected after 24 hrs. The $^{35}$S-labeled HepG2 culture supernatant (300 μL) was incubated with 16 μg of purified recombinant TSG-6 protein or with buffer for 1 hr. at 37° C. Samples were precleared with 150 μL of 10% SAC. Rabbit anti-TSG-6 antiserum or preimmune serum from the same rabbit (5 μL) was added to the supernatants and incubated for 3 hrs. at 37° C. Thereafter, 150 μL of 10% SAC was added and incubated for 30 min. at room temperature. The supernatants were removed, and the pellets were washed 3 times with 1 mL of 20 mM Tris, pH 7.5, 0.5 M NaCl containing 0.02% Tween-20. Pellets were resuspended in 40 µL of SDS-PAGE buffer (reducing) and incubated for 3 min. in a boiling water bath. The supernatants were removed and analyzed by SDS-PAGE on lot polyacrylamide (PAA) gels and fluorography.
Partial Purification of TSG-6 Binding Protein from Human Serum for N-Terminal Microsequencing.

Protein precipitated between 40% and 55% saturation with ammonium sulfate from 40 mL of fresh human serum was dissolved in 10 mL of PBS and dialyzed against 50 mM $KH_2PO_4$, pH 7.0, 50 mM NaCl. Four aliquots were passed through Affini-filter cartridges for albumin removal (Affinity Technology). Each cartridge was washed with 5 mL of the same buffer and eluted with 5 mL of 50 mM $KH_2PO_4$, pH 7.0, 0.5 M NaCl. The eluates of four cartridges were pooled, dialyzed against 20 mM Tris, pH 7.5, 50 mM NaCl, and loaded on a MonoQ column (HR5/5, Pharmacia) using a Pharmacia FPLC system. Protein was eluted with a linear gradient (16 mL) from 50 mM to 1 M NaCl in 50 mM Tris, pH 7.5. Fractions containing TSG-6 binding activity were pooled and concentrated in Centricon-10 units to a final volume of 200 µL. This material was further separated by FPLC on a Superdex 200 column (HR 10/30). The column was equilibrated with 50 mM $Na_2HPO_4$, pH 7.0, 150 mM NaCl and run at a flow rate of 0.5 mL/min. Fractions containing TSG-6 binding activity were pooled and concentrated in Centricon-10 units. The material was further separated by SDS-PAGE under reducing conditions on a 4–15% PAA gel and transferred in methanol-free transfer buffer at 200 mA for 1 hr. to a PVDF membrane. Staining with Coomassie Blue R250 revealed only one protein band greater than 200 kDa which was used for microsequencing.
Purification of IαI from Human Serum.

IαI was purified from human serum, according to Salier et al., *Anal. Biochem.* 109:273–283 (1980), with some modifications. FPLC on Q Sepharose Fast Flow was used instead of DEAE-Sephacel chromatography. Chelating Sepharose Fast Flow was used for zinc chelate chromatography. Phenyl Superose was used for hydrophobic chromatography and Superdex 200 was used for size-exclusion chromatography instead of Sephacryl-300. The IαI recovered was essentially pure as judged by SDS-PAGE and silver staining.
Protein Sequencing.

Coomassie Blue-stained protein bands on the PVDF membranes were cut from the blots and placed directly into a micro-cartridge on an Applied Biosystems Model 473A protein sequencer. Automated Edman degradations were performed using standard cycles with gas phase delivery of trifluoroacetic acid (TFA). Data collection and reduction were performed using Applied Biosystems Model 610 software.
Microsequencing of the TSG-6/IαI Complex.

Purified recombinant TSG-6 (2.5 µg) was incubated with 2.6 µg of IαI purified from human serum for 1 hr. at 37° C. After SDS-PAGE in an 80% PAA gel under reducing conditions, protein was transferred to a PVDF membrane in methanol-free transfer buffer at 200 mA for 1 hr. The membrane was stained with Coomassie Blue R250, and the newly formed 120-kDa band (not present in the IαI or TSG-6 preparation) was excised for microsequencing.

RESULTS

Binding of TSG-6 Protein to a Protein Present in Manmalian Sera and in Supernatants of Human HepG2 Hepatoma Cells.

Fetal bovine serum, serum-free supernatants of human HepG2 cells, or mouse serum were incubated in the absence or presence of recombinant human TSG-6 for 1 hr. at 37° C. and all samples were then subjected to Western blot analysis with rabbit antiserum to TSG-6. Western blot analysis of serum-free culture supernatant of TN-5B insect cells infected with recombinant Baculovirus encoding human TSG-6 revealed the presence of a 32-kDa band reactive with antibody to TSG-6. Recombinant human TSG-6 protein produced in insect cells migrates somewhat faster than the 35-kDa TSG-6 protein from human cells (Wisniewski et al., supra, 1993) possibly due to a different extent of glycosylation. A second band recognized by antibody against TSG-6, with the apparent molecular mass of 29 kDa, probably represent unglycosylated TSG-6 protein present in variable amounts in preparations of TSG-6 protein from insect cells infected with recombinant Baculovirus. When TSG-6 containing culture supernatants were incubated at 37° C. in the presence of fetal bovine serum, mouse serum, or serum-free culture supernatant of human HepG2 hepatoma cells, an additional 120-kDa band became readily apparent. A band of identical electrophoretic mobility appeared after incubation of recombinant TSG-6 protein with human or rabbit serum.
The 120-kDa Band Represents a Complex of TSG-6 with a Distinct Protein.

In order to show that the newly formed 120-kDa band revealed by Western blot analysis is indeed a complex of TSG-6 with a distinct protein, and not a TSG-6 oligomer whose formation is promoted by serum, we employed immunoprecipitation. When a supernatant from HepG2 cells cultured in serum-free medium in the presence of $^{35}S$-methionine was incubated with unlabeled purified recombinant TSG-6 protein and immunoprecipitated with a rabbit antiserum to TSG-6, a labeled 120-kDa molecule was precipitated and analyzed by SDS-PAGE in an 10% PAA gel and fluorography. This immunoprecipitation was specific because incubation with pre-immune serum from the same rabbit or incubation of $^{35}S$-labeled HepG2 supernatants with immune serum in the absence of TSG-6 protein failed to precipitate a labeled 120-kDa molecule. [$^{35}S$]Methionine incorporation into a molecule specifically recognized by an antibody to TSG-6 indicates that the 120-kDa molecule is indeed a complex of TSG-6 protein with another distinct protein that is constitutively produced and secreted by human HepG2 cells.
Partial Purification and Identification of the TSG-6 Binding Protein from Human Serum.

Fractionation of normal human serum by ammonium sulfate precipitation showed that proteins precipitated between 40% and 55% saturation contained most of the TSG-6 binding activity, although significant binding was also detected in the fraction precipitated at an ammonium sulfate saturation of 40%. The purification procedure used for the isolation of the binding protein and the Western blot-based assay used for the detection of TSG-6 binding protein are described under Experimental Procedures. During Affini-filter chromatography, most of the TSG-6 binding activity eluted at 0.5 M NaCl together with residual albumin. FPLC on a MonoQ column proved to be very efficient for further purification of the TSG-6 binding protein. SDS-PAGE followed by silver staining revealed that incubation of fractions of a partially purified preparation of TSG-6 binding protein from MonoQ-FPLC with recombinant TSG-6 protein resulted in the partial disappearance of a >200-kDa band and the appearance of a new band at 120 kDa (samples were separated by SDS-PAGE in an 10% PAA gel under reducing conditions and silver stained). This finding suggested that the human TSG-6 binding protein is greater than 200 kDa in size and hence considerably greater than its complex with TSG-6. During FPLC on Superdex 200, the TSG-6 binding protein eluted with a retention volume corresponding to a molecular mass of about 270 kDa. Fractions containing TSG-6 binding activity were concentrated about 80-fold before SDS-PAGE was performed on 4–15% PAA gradient gels or 8% PAA gels under reducing conditions. Proteins were transferred electrophoretically to PVDF membranes. CBB staining revealed the presence of only one band greater than 200 kDa which was cut for microsequencing.

Microsequencing of the TSG-6 binding protein resulted in double signals for the first five cycles and one signal for each of the following seven cycles. Comparison of the resulting sequences with sequence stored in protein databases revealed that they identify two of the three chains of the human inter-α-(trypsin) inhibitor (IαI): the bikunin chain of IαI was presented by its 12 N-terminal amino acids, whereas the heavy chain 2 (HC2) was represented by its 5 N-terminal amino acids (Table 2). It is noteworthy that $Ser^{10}$ of the bikunin chain could not be identified. No signals corresponding to the heavy chain 1 (HC1) of IαI were retrieved. The microsequencing data along with the molecular mass of ~250 kDa (determined by SDS-PAGE) indicate that the TSG-6 binding protein is IαI rather than inter-α-like-inhibitor (IαLI) whose molecular mass is 130–140 kDa (Enghild et al., *J. Biol. Chem.* 264:15975–15981 (1989); Rouet et al., *Biol. Chem. Hoppe-Seyler* 373:1019–1024 (1992)). Subsequent microsequencing of another preparation of IαI purified from human serum allowed the identification of HC1 besides HC2 and bikunin. However, the detected amount of HC1 was substantially lower than that of the two other chains on a molar basis.

TABLE 2

N-Terminal Amino Acid Sequence of the Human TSG-6 Binding Protein Determined by Microsequencing

| Position | Amino Acid Residues | |
| --- | --- | --- |
| 1 | Ala | Ser |
| 2 | Val | Leu |
| 3 | Leu | Pro |
| 4 | Pro | Glu |
| 5 | Gln | Gly |
| 6 | Glu | —a |
| 7 | Glu | — |
| 8 | Glu | — |
| 9 | Gly | — |
| 10 | Xaa | — |
| 11 | Gly | — |
| 12 | Gly | — |
| | (SEQ ID NO:2) | (SEQ ID NO:3) | aNot determined

Rapid Complex Formation between Recombinant TSG-6 Protein and IαI Purified from Human Serum at 37° C. The 120-kDa TSG-6/IαI complex formed readily when purified TSG-6 protein and purified IαI were incubated together for 2, 5, 10, 15, 30, or 60 min. at 37° C., but not at 020 C. when incubated for 60 min. At 37° C., complex formation was detectable within 2 min. (Western blot analysis of reaction mixtures separated by SDS-PAGE using rabbit anti-TSG-6 serum), and the reaction appeared to be complete by 10 min. At 0° C., however, little or no TSG-6/IαI complex was formed thin 1 hr. Purified IαI was incubated in the absence or presence of purified TSG-6 protein at 37° C. for 10 min. and all samples were separated by SDS-PAGE on 8% PAA under reducing conditions. Mono-specific rabbit antisera against either TSG-6 protein or IαI detect the 120-kDa complex in Western blots, indicating the presence of both TSG-6 and IαI epitopes in a stable complex. Besides the formation of the TSG-6/IαI complex of 120 kDa, incubation of TSG-6 protein with IαI resulted in the appearance of yet another band with a molecular mass of ~130 kDa which was detected by anti-IαI but not by anti-TSG-6. This IαI derivative appears to be a byproduct of the reaction of TSG-6 with IαI. It should be noted that the 120-kDa TSG-6/IαI complex is formed by purified TSG-6 and IαI proteins in the apparent absence of other proteins.

Composition of the TSG-6/IαI Complex.

The 120-kDa complex, formed by incubating together purified TSG-6 protein and IαI, was isolated and identified by SDS-PAGE in an 8% PAA gel, electrotransfer to a PVDF membrane, and CBB staining. Microsequencing of the isolated band corresponding to the complex revealed the presence of TSG-6 (shown below in Table 3 as an amino acid sequence corresponding to amino acids 18–27 of SEQ ID NO:1) protein, bikunin, and HC2 of IαI in nearly equimolar ratios (Table 3). Interestingly, $Ser^{10}$ of the bikunin chain, which was not detectable during microsequencing of IαI (see Table 2), was found in an equimolar amount in the TSG-6/IαI complex. The unexpected appearance of a serine residue in position 10 could reflect the presence of an additional chain or partial modification of one or more N-termini. A less likely possibility is that $Ser^{10}$ of the bikunin chain, which is glycosylated in IαI, might become deglycosylated in the process of TSG-6/IαI complex formation.

TABLE 3

N-Terminal Amino Acid Sequences of the TSG-6/IαI Complex Determined by Microsequencing

| | Amino Acid Residues | | | Yield (pmol of phenylthiohydantoin (PTH)) | | |
| --- | --- | --- | --- | --- | --- | --- |
| Position | Bikunin | HC2 | TSG-6 | | | |
| 1 | Ala | Ser | Trp | 10 | 12 | 15 |
| 2 | Val | Leu | Gly | 10 | 12 | 12 |
| 3 | Leu | Pro | Phe | 9 | 11 | 9 |
| 4 | Pro | Gly | Lys | 9 | 15 | 8 |
| 5 | Gln | Glu | Asp | 7 | 12 | 13 |
| 6 | Glu | Ser | Gly | 11 | 8 | 13 |
| 7 | Glu | Glu | Ile | 13 | | 9 |
| 8 | Glu | Glu | Phe | 15 | | 9 |
| 9 | Gly | Met | His | 11 | 9 | 6 |
| 10 | Ser | Met | Asn | 8 | 12 | 13 |
| | SEQ ID NO:4 | SEQ ID NO:5 | SEQ ID NO:1 (18–27) | | | |

The Stable Crosslink in the TSG-6/IαI Complex is Provided by a Glycosaminoglycan Chain.

The stability of the 120 kDa TSG-6/IαI complex during SDS-PACE under reducing conditions raises the question of the nature of the interaction between TSG-6 and the other components of the complex. Addition of 8 M urea before SDS-PAGE did not affect the 120-kDa complex. The effect of treatment with 8 M guanidine hydrochloride could not be fully evaluated because the detectability of both the TSG-6 band and the TSG-6/IαI in Western blots was significantly diminished. However, the TSG-6/IαI complex was still detectable after treatment with 8 M guanidine hydrochloride. Taken together, these data reflect the high stability of the TSG-6/IαI complex, and the formation of a covalent bond cannot be ruled out.

It is known that the three polypeptide chains of IαI are cross-linked by a chondroitin sulfate chain (Enghild et al., *J. Biol. Chem.* 264:, 15975–15981 (1989); Jenssen et al., *FEBS Lett*, 230:195–200 (1988); Balduyck et al., *Biol. Chem.*

*Hoppe-Seyler* 370:329–336 (1989)). It has been shown that bikunin, HC2 of IαLI, and HC3 of pre-α-inhibitor (PαI) are covalently bound to chondroitin 4-sulfate (Enghild et al., *J. Biol. Chem.* 264:, 15975–15981 (1989); Enghild et al., supra, (1991); Enghlid et al., *J. Biol. Chem.* 268:8711–8716 (1993). To determine if cross-linking via chondroitin sulfate is also required for the stability of the TSG-6/IαI complex, purified TSG-6 protein and partially purified IαI were first incubated together to allow the formation of the complex and then treated with 800 milliunits of chondroitin sulfate ABC lyase from Proteus vulgaris or 1.6 units of hyaluronidase from Streptomyces hyalurolyticus. Treatment with chondroitin sulfate ABC lyase resulted in complete disappearance of the complex as analyzed by Western blotting with anti-TSG-6 antibody whereas hyaluronidase has no effect.

Chondroitin Sulfate Associated with IαI is Required for the Formation of the TSG-6/IαI Complex.

In order to determine the effect of chondroitin sulfate ABC lyase on either TSG-6 protein or IαI separately, purified TSG-6 protein and purified IαI from human serum were incubated with a limited amount of chondroitinase for 16 hrs. and then mixed with untreated IαI or TSG-6 protein, respectively. Western blotting with anti-TSG-6 antibody revealed that IαI preincubated with chondroitin sulfate ABC lyase was no longer able to form a complex with untreated TSG-6 protein. On the other hand, pretreatment with chondroitinase had little effect on the ability of TSG-6 protein to react with untreated IαI. A slight decrease of the amount of TSG-6/IαI complex formed by chondrioitinase-pretreated TSG-6 can be explained by carry-over of the enzyme into the final TSG-6-IαI incubation mixture because the chondroitinase could not be selectively inactivated. Limiting chondroitinase activity to the necessary minimum was essential in this experiment in order to prevent IαI inactivation during the final incubation. This finding suggests that IαI, but not TSG-6 protein, has a chondroitinase-sensitive structure required for the formation of the TSG-6-IαI complex.

Discussion

It has previously been shown that TSG-6 synthesis is rapidly induced in human diploid fibroblasts and peripheral blood mononuclear cells after stimulation with the inflammatory cytokines TNF and IL-1 (Lee et al., *Mol. Cell. Biol.* 10:1982–1988, (1990), Lee et al., *J. Biol. Chem.* 268, 6154–6160, (1993); Wisniewski et al., supra, 1993). The affinity of TSG-6 protein for hyaluronan suggests a possible association with the extracellular matrix and cartilage (Lee et al., supra, 1992). High levels of TSG-6 protein in the synovial fluid of patients with rheumatoid arthritis and constitutive TSG-6 expression by cultured synovial cells from rheumatoid joints in vitro that was further enhanced by TNF and IL-1, suggested a role for TSG-6 in inflammatory diseases of connective tissue and cartilage (Wisniewski et al., supra, 1993). The results show that recombinant human TSG-6 protein is readily incorporated into a stable 120 kDa complex if incubated with human, fetal bovine, rabbit, or mouse serum. Isolation and microsequencing of the human TSG-6 binding protein allowed its identification as IαI, an extensively studied serum protein.

IαI is a complex protein in which the bikunin chain is linked to HC1 and HC2 (Enghild et al., supra, (1989); Gebhard et al., supra, (1990); Rouet et al., supra, (1992)). Yet, sequence analysis of the TSG-6 binding protein purified from human serum revealed only the bikunin chain and HC2 (Table 2), and no indication for the presence of HC1 was obtained. Subsequent sequencing of another preparation of IαI purified from human serum resulted in the detection of very weak signals for the sequence of HC1, corresponding to about one-tenth of the other two chains on a molar basis. Other investigators who reported N-terminal sequencing data for IαI also received incomplete and divergent sequences for HC1 when sequencing the unmodified IαI molecule (Enghild et al., supra, (1989); Jessen et al., *FEBS Lett.* 320, 195–200 (1988); Malki et al., *Biol. Chem. Hoppe-Seyler* 373, 1009–1018 (1992)). Nevertheless, little doubt exists that the TSG-6 binding proteins is IαI because IαI is the only member of this protein family with a molecular mass greater than 200 kDa. IαLI, which consists of bikunin and HC2, the two chains we detected by microsequencing, has a molecular mass of only 130–140 kDa (Enghild et al., supra, 1989; Rouet et al., supra, 1992). In addition, IαI was found to form what appears to be the same 120 kDa complex with TSG-6 proteins whole serum. While there is no doubt that IαI is the binding TSG-6 protein we have isolated, it is possible that IαLI or PαI also can bind TSG-6 protein.

Evidence that the reaction between TSG-6 and IαI indeed yields a complex of TSG-6 with one or more polypeptide chains of IαI is provided by the immunoprecipitation data. Further information about the composition of the TSG-6/IαI complex is derived from Western blot analysis. Antisera specific for either TSG-6 protein or IαI detected a 120 kDa band newly formed upon incubation of TSG-6 protein and IαI with each other, suggesting the presence of TSG-6 and IαI epitopes in the complex. This was confirmed by microsequencing of the TSG-6/IαI complex (Table 3) which revealed the presence of three chains: TSG-6 protein, bikunin, and HC2. The signals of all three chains are represented in nearly equimolar amounts, suggesting that the complex contains one of each polypeptide chain. No signals corresponding to HC1 could be detected. The molecular mass of the complex is surprisingly low if one considers the molecular masses of the incorporated polypeptides. HC2 has a molecular mass of 70 kDa (Enghild et al., *J. Biol. Chem.* 264, 15975–15981 (1989)), the reported molecular mass of bikunin is 26–70 kDa depending on the extent of glycosylation (Gebhard et al., supra, (1990); Rouet et al., supra, (1992)), and that of recombinant TSG-6 protein is 32 kDa. The fact that the apparent molecular mass of the 120 kDa complex is less than the sum of its components suggests that some additional modifications, such as deglycosylation or limited proteolytic cleavage, might take place. Alternatively, changes of the gross structure of the complex due to incorporation of TSG-6 could have a substantial effect on its apparent molecular mass.

The unusual stability of the TSG-6/IαI complex raises the question of the nature of the bonds linking its components. The resistance of the complex to boiling in 2% SDS and 5% β-mercaptoethanol as well as to 8 M urea makes any noncovalent hydrophobic or hydrophilic bond unlikely. In addition, the strict temperature dependence of TSG-6/IαI complex formation suggests that the reaction involves an activated transition state and supports the notion that a covalent bond is formed. However, an unusually stable noncovalent association of TSG-6 with the glycosaminoglycan chain of the complex cannot be ruled out. The polypeptide chains of IαI are cross-linked by chondroitin 4-sulfate chain (Enghild et al., supra, (1989); Jessen et al., *FEBS Lett.* 320, 195–200 (1988); Balduyck et al., *Biol. Chem. Hoppe-Seyler* 370, 329–336 (1989)). The sensitivity of the TSG-6/IαI complex to chondroitin sulfate ABC lyase and the inability of chondroitinase-pretreated IαI to form the complex suggests that the chondroitin 4-sulfate chain cross-linking the polypeptide chains of IαI is also required for the formation of the 120 kDa complex. It has been shown that the chondroitin 4-sulfate chain of IαI is bound to $Ser^{10}$ of bikunin via a common Gal-Gal-Xyl oligosaccharide (Enghild et al., supra, (1989); Enghild et al., supra, (1991); Chirat et al., supra, (1991)). An unusual ester bond has been shown to cross-link the α-carboxylic a group of the HC2 C-terminal $Asp^{648}$ of IαLI to C-6 of an internal N-acetyl-galactosamine of the chondroitin 4-sulfate chain (Enghild et al., supra, (1993)). A similar bond cross-links the C-terminal $Asp^{618}$ of HC3 to chondroitin 4-sulfate in PαI (Enghild et al., supra, (1991); Enghild et al., supra, (1993)). Analysis of the cDNAs of the three heavy chains showed that all have the conserved consensus sequence Val-Xaa-Xaa-Asp-Pro-His-Ile-Ile (SEQ ID NO:6), supposed to determine the cleavage site for the C-terminal propeptide (Bourguignon et al., *Eur. J. Biochem.* 212, 771–776 (1993)) after the aspartic acid residue. This cleavage generates the free α-carboxylic group of the now C-terminal aspartic acid residue which forms the ester bond to an internal N-acetylgalactosamine of chondroitin 4-sulfate, two reactions that may be closely coupled. Interestingly, TSG-6 also features a core of the consensus sequence Val-Xaa-Xaa-Asp-$Pro^{249}$ (corresponding to amino acid residues 1–5 of SEQ ID NO:6). Hence, it is conceivable that TSG-6 forms a direct covalent bond to the chondroitin 4-sulfate chain of IαI. Additional studies are required to determine the molecular structures formed and the exact nature of the interactions leading to the formation of the exceedingly stable TSG-6/IαI complex.

EXAMPLE II

In this example, the question of whether formation of the TSG-6/IαI complex would affect the protease inhibitory activity of IαI is addressed. of specific interest was the ability of TSG-6 to influence the protease inhibitory activity of IαI against plasmin, which besides its role in fibrinolysis, has an important function in the proteinase cascade activated in inflammation and, through its ability to activate matrix metalloproteinases (MMP) is involved in extracellular matrix degradation (Opdenakker et al., *Cytokine* 4:251–258, 1992; Matrisian, *Bioessays* 14:455–463, 1992; Murphy et al., *Matrix Supplement* 1:224–230, 1992; Alexander et al., In *Cell Biology of Extracellular Matrix*, E. D. Hay (ed.), Plenum Press, New York, 255–302, 1991). Plasmin itself is activated by proteolytic cleavage of plasminogen by tissue plasminogen activator (t-PA) and urokinase type plasminogen activator (u-PA). Interestingly, plasmin is able to activate the latent precursor of u-PA (Bernik et al., *J. Amer. Med. Womens Assoc.* 31:465–472, 1976), and this mutual activation of plasminogen/plasmin and u-PA generates a positive feedback loop. The experiments in this example revealed that TSG-6 produces a marked increase in the protease-inhibitory action of IαI against plasmin. Because an inhibition of the protease cascade would be expected to lead to an anti-inflammatory effect, the effect of TSG-6 was tested in the murine air pouch model of carrageenan- or IL-1-induced acute inflammation. TSG-6 protein exerted a potent anti-inflammatory effect as demonstrated by an inhibition of neutrophil infiltration into the air pouch. Site-directed mutagenesis was used to address the question of whether the synergistic effect of TSG-6 and IαI on plasmin activity and the anti-inflammatory effect are causally related. Two mutant TSG-6 proteins with single amino acid substitutions that lost the ability to potentiate the plasmin-inhibitory activity of IαI also showed a complete or partial loss of the anti-inflammatory action, suggesting that these two functions of TSG-6 protein are related.

EXPERIMENTAL PROCEDURES

Expression and Purification of Recombinant Human TSG-6 Protein.

TSG-6 protein was produced in BTI-TN-5Bl-4 insect cells after infection with recombinant nuclear polyhedrosis virus and purified from culture supernatants as described in Example I. Preparations of recombinant human (rhu) TSG-6 protein used in the experiments were ≧95% pure, as judged by SDS-PAGE analysis.

Purification of Inter-α-inhibitor from Human Plasma.

Human IαI inhibitor was purified from plasma essentially as described in Example I with the exception that zinc chelate chromatography was replaced by chromatography on Blue Sepharose (Pharmacia), using a linear NaCl-gradient (50 mM to 1 M) in 20 mM Tris buffer, pH 7.4 for elution. Purified IαI from human plasma was more stable than IαI isolated from serum and could be stored frozen at −70° C.

Site-directed Mutagenesis.

Site-directed mutagenesis was carried out according to Deng et al. (*Analytical Biochemistry* 200:81–88, 1992) using the Transformer™ site-directed mutagenesis kit from Clontech Laboratories, Inc., Palo Alto, Calif. The TSG-6 cDNA was subcloned into the Baculovirus transfer vector pBac-PAK8 (Clontech Laboratories) and the resulting construct pBPT6 was used for site-directed mutagenesis. For the generation of $pBPTG^{K41}$ and $pBPT6^{E48}$, the selection primer SEQ ID NO:7, the mutagenic primers SEQ ID NO:8 (to generate $pBPT6^{K41}$) and SEQ ID NO:9 (to generate $pBPT6^{E48}$) were used. XhoI (New England Biolabs, Beverly, Mass.) was used for the selective restriction. The presence of the point mutations was confirmed by DNA-sequencing of the mutated plasmids. Recombinant nuclear polyhedrosis virus (NPV) was generated by cotransfection of either $pBPT6^{K41}$ or $pBPT6^{E48}$ together with pBacPAK6 Bsu36I-digested viral DNA (Clontech Laboratories) into Sf9 insect cells using the Clontech Laboratories lipofectin transfection procedure. Recombinant NPV was isolated from viral plaques in soft agar and propagated in Sf9 cells. Recombinant mutant proteins were purified as described for wild-type TSG-6 protein.

Experimental Inflammation in the Murine Air Pouch Model.

Six-week-old female BALB/c mice were purchased from Taconic Farms, Inc., Germantown, N.Y. Air pouches were induced on the back of the mice by three subcutaneous injections of air every second day. The air pouch experiments were essentially carried out as described previously (Cronstein et al., *J. Clin. Invest.* 92:2675–2682, 1993). To induce an acute inflammation, 1 ml of a 2% (w/v) carrageenan solution in saline or 1 ml saline containing 40 ng recombinant murine IL-1β was injected directly into the air pouch. When mice were treated with various amounts of rhuTSG-6 protein or mutant TSG-6 proteins, these were injected together with the inflammatory stimulus directly into the air pouch. After 4 h the mice were euthanized, 2 ml saline was injected into each air pouch and the exudate aspirated. Aliquots were diluted with saline and the cells counted. Wright-Giemsa stained smears of air pouch exudates from untreated mice revealed the presence of ≧95% PMN 4 h after the inflammatory stimulus. Air pouch exudates were also analyzed for the presence of TSG-6 protein by Western blotting as described earlier (Wisniewski et al., supra, 1993). Some air pouches were dissected and processed for histological examination as described by Cronstein et al., supra, 1993. Excell 5.0 software (Microsoft Inc., Bothell, Wash.) was used for statistical analysis by two-sided t-test.

Plasmin Assay.

Plasmin assays were carried out by using Tosyl-gly-pro-lys-4-nitranilide acetate (Chromozym$^R$PL, Boehringer Mannheim GmbH, Mannheim, Germany) as a chromogenic substrate in 10 mM HEPES, pH 7.4, 150 mM NaCl, 0.02% Tween-20, essentially recommended by the manufacturer. Reaction mixtures were incubated at 37° C. for various time periods after which the degree of proteolysis was determined spectrophotometrically at 450 nm. IαI and/or TSG-6 were preincubated with human plasmin (Boehringer Mannheim GmbH) for 10 min at 37° C. before the addition of the substrate to allow the formation of plasmin-inhibitor complexes. If TSG-6 and IαI were used together, they were preincubated for 30 min at 37° C. to allow the formation of the stable TSG-6/IαI complex. The final concentrations in the assay were 197 μM Chromozym$^R$PL, 3.4 nM plasmin, 18 nM IαI, and 44.3 nM to 369.4 nM TSG-6 protein or the respective mutant proteins.

TSG-6 Synergizes with IαI to Inhibit Proteolysis by Plasmin.

It was shown in Example I that TSG-6 protein forms a stable complex with components of the serine protease inhibitor, IαI. The 120 kDa complex formed upon interaction of TSG-6 with IαI includes the bikunin chain of IαI that is responsible for the serine protease inhibitory activity of IαI (Morii et al., *Biol. Chem. Hoppe-Seyler* 366:19–21, 1985; Enghild et al., supra, 1989; Gebhard et al., supra, 1990). The functional consequences of the formation of the complex between TSG-6 and IαI were not previously examined. In view of the important roles of plasmin in fibrinolysis and inflammation, the question of whether TSG-6 affects the inhibition of plasmin activity by IαI was addressed.

Figure 2:
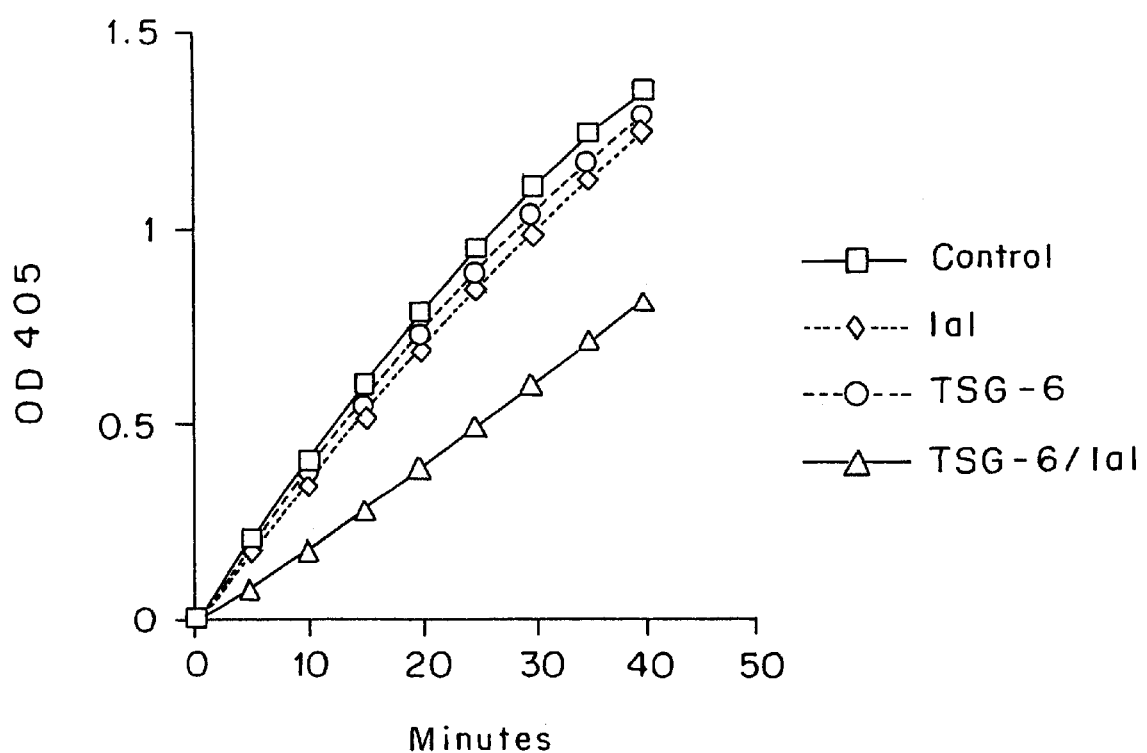
FIG. 2 shows the effect of TSG-6 protein on the anti-plasmin activity of IαI. Plasmin activity was assayed with 3.4 nM plasmin alone (control), or in the presence of 18 nM IαI (IαI), 369 nM TSG-6 protein or both 18 nM IαI and 369 nM IαI (TSG-6/IαI). The protease activity of plasmin was assayed as described in Example II where TSG-6 protein potentiates the inhibition of plasmin activity by a subeffective concentration of IαI.

The anti-protease activity of IαI was examined by assaying its ability to inhibit plasmin-caused degradation of a synthetic substrate. IαI alone showed a modest dose-dependent inhibitory effect on plasmin activity (FIG. 1). Increasing the concentration of IαI over the highest concentration used in the experiment shown in FIG. 1 (with plasmin concentration being kept constant) did not lead to a marked further increase inhibition. TSG-6 protein alone has virtually no effect on plasmin activity in this assay at a 108-fold molar excess. However, TSG-6 protein and IαI showed a strong synergistic effect resulting in a potent inhibition of plasmin activity (FIG. 2). These results suggest that the complex of TSG-6 with components of IαI is a stronger inhibitor of plasmin activity than intact IαI alone.

Anti-inflammatory Effect of TSG-6 Protein in a Murine Model of Acute Inflammation.

Figure 3:
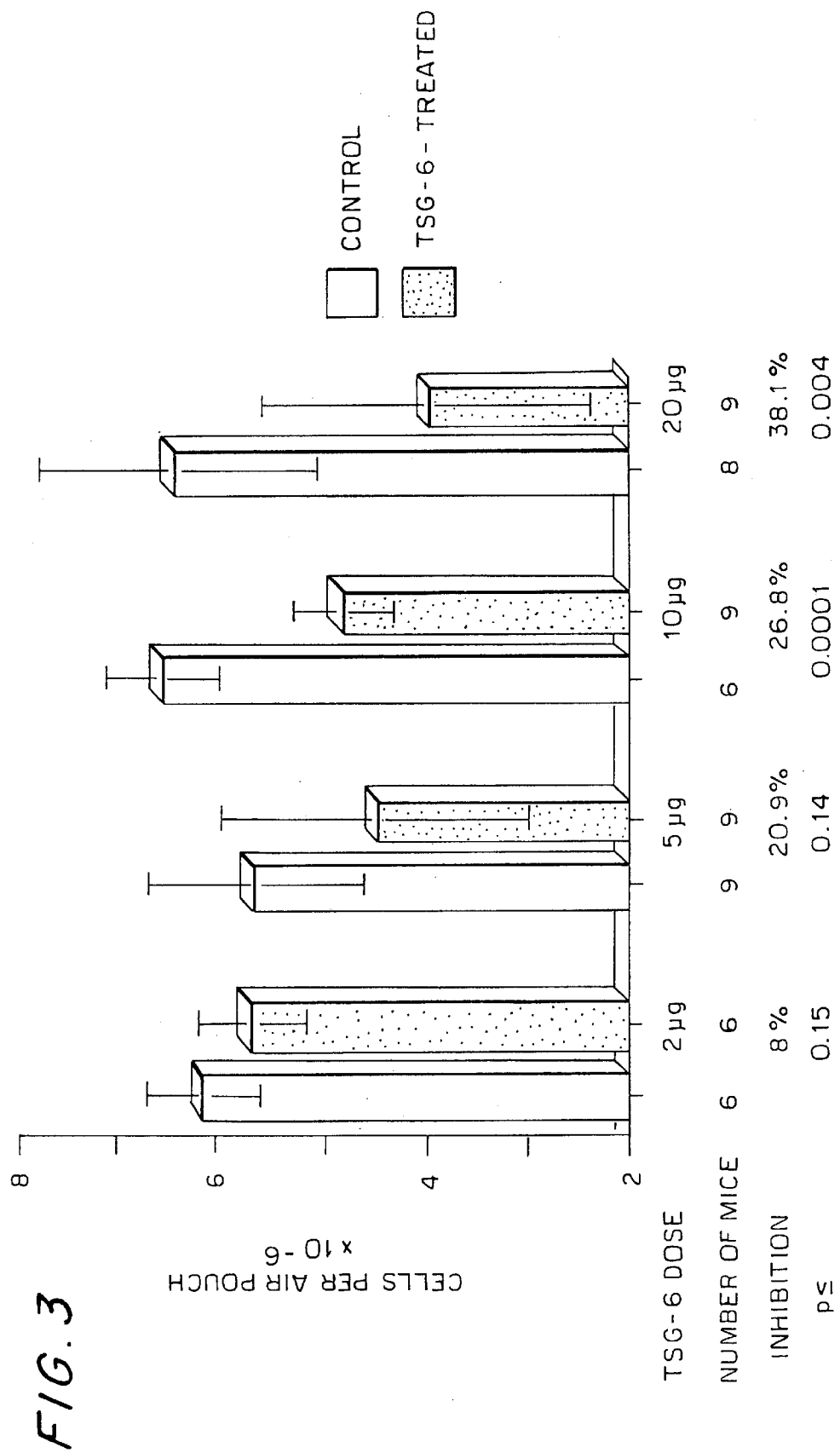
FIG. 3 shows the inhibition of carrageenan-induced cellular infiltration by TSG-6 in the murine air pouch where the number of cells infiltrating air pouches 4 h after injection with carrageenan alone (empty bars) or with carrageenan and rhuTSG-6 protein (stippled bars) are shown. TSG-6 protein doses (injected with carrageenan), the numbers of mice per group, and percent inhibition of cellular infiltration are indicated. The p-values were determined by two-sided t-test.
Figure 4:
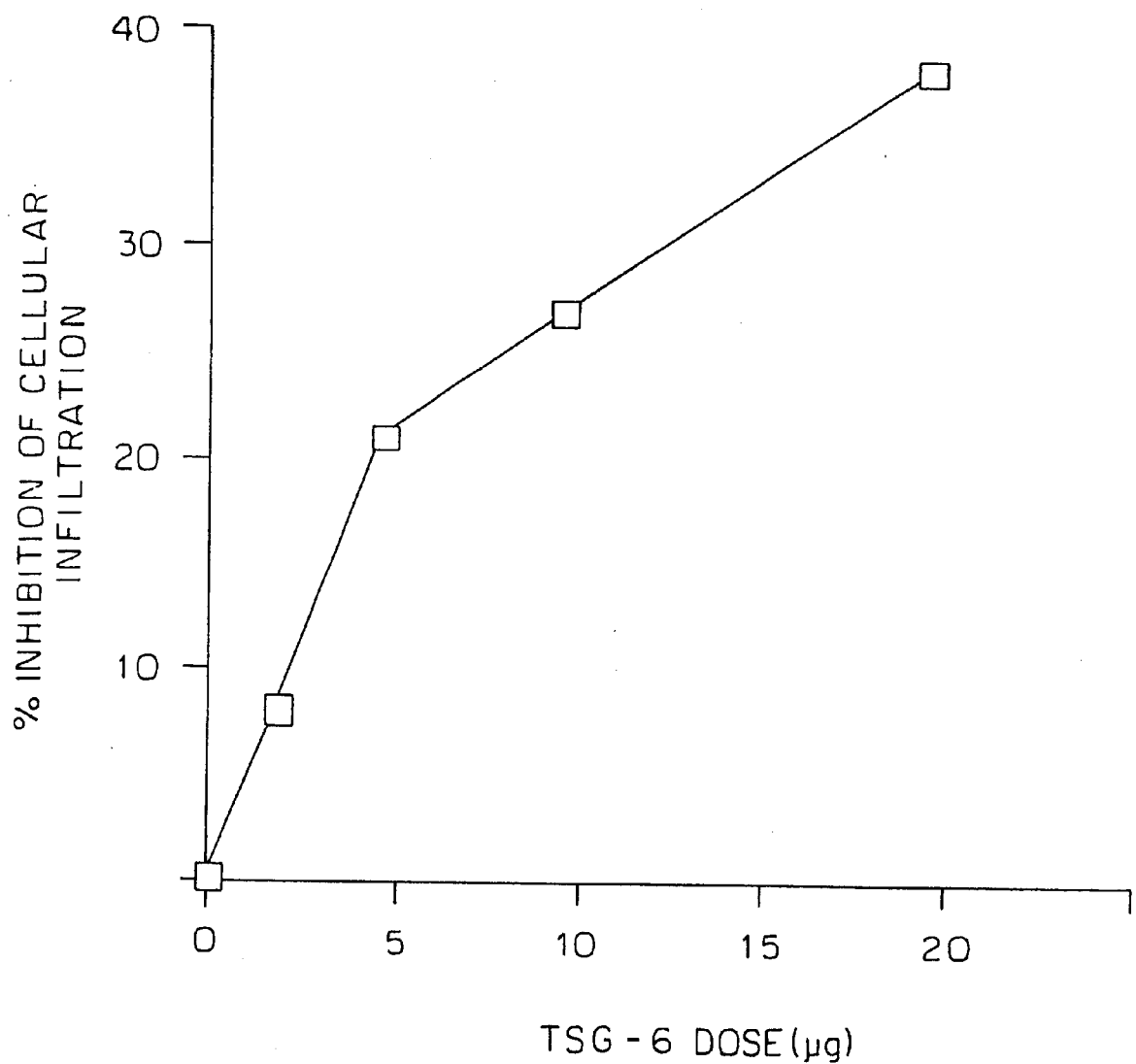
FIG. 4 shows the percent inhibition of the cellular infiltration with increasing doses of rhuTSG-6 (same data as in FIG. 3).
Figure 5:
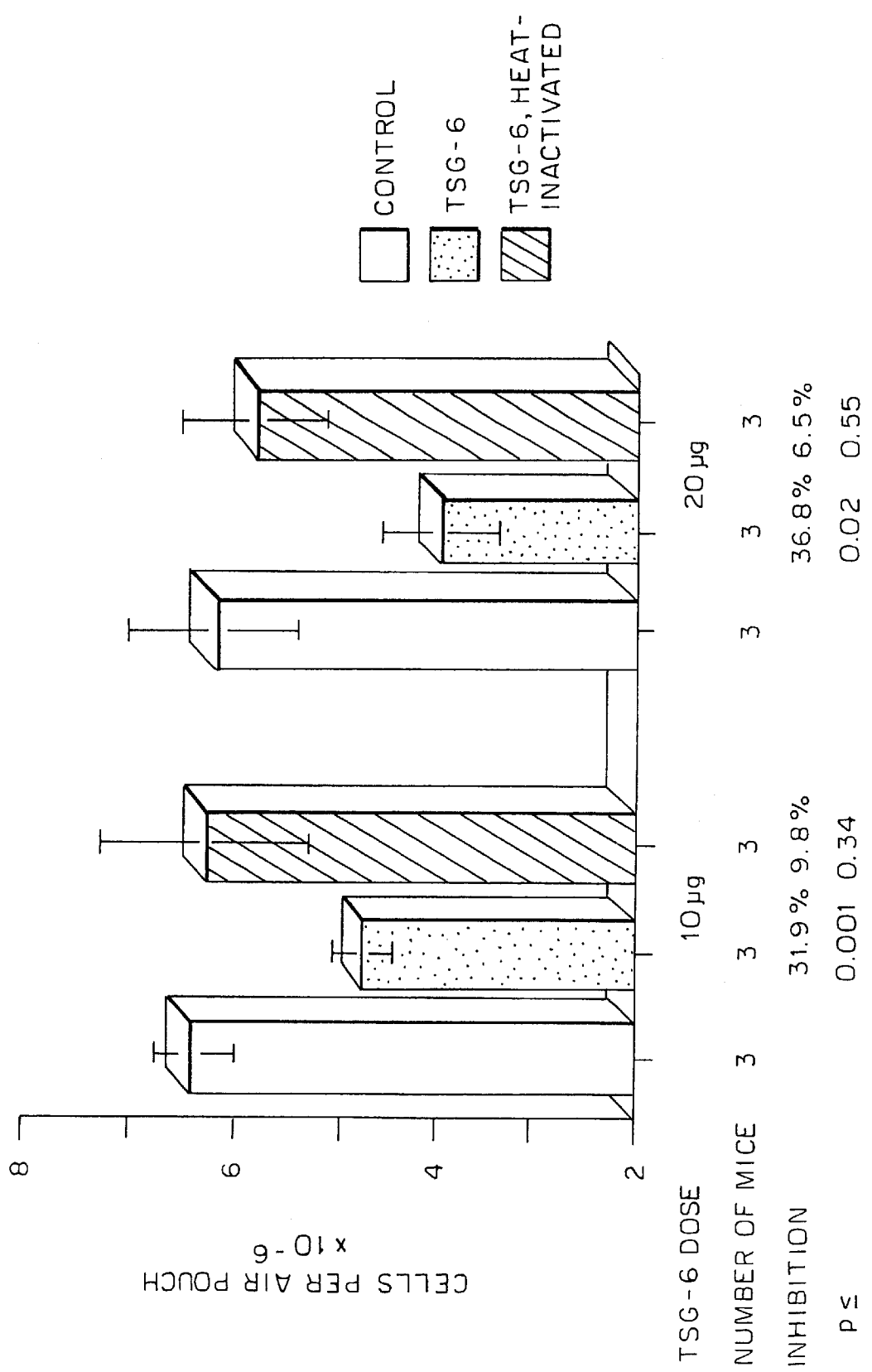
FIG. 5 shows that the anti-inflammatory activity of TSG-6 protein is destroyed by boiling. The number of infiltrating cells 4 h after injection of air pouches with carrageenan are shown in control mice (empty bars), in mice treated with carrageenan together with rhuTSG-6 protein (stippled bars), or in mice treated with carrageenan and rhuTSG-6 heated for 3 min at 100° C. (hatched bars). The doses of TSG-6 protein injected, the number of mice, and the percent inhibition of the cellular infiltration are indicated. The p-values were determined by two-sided t-test.

The synergistic inhibitory effect of TSG-6 protein and IαI on plasmin activity suggested that this interaction could affect the protease network activated in inflammation which is responsible for local extracellular matrix degradation associated with cellular infiltration. To directly address the question whether TSG-6 can modulate the inflammatory response in vivo, the effect of TSG-6 protein on carrageenan-induced inflammation in the murine air pouch model (Magilavy, *Clinical Orthopaedics & Related Research* 259:38–45, 1990) was tested. Air pouches were generated by repeated injection of air under the skin on the back of the mice. TSG-6 protein injected directly into the air pouch at the same time as carrageenan significantly reduced the number of cells infiltrating the air pouch as determined at 4 h after carrageenan administration (FIGS. 3 and 4). The inhibitory effect of TSG-6 protein was dose-dependent, with a dose of 10 μg required to produce a statistically significant inhibition under the conditions employed. The administration of TSG-6 protein at doses greater than 20 μg did not further increase the anti-inflammatory effect. Boiling purified TSG-6 protein for 3 min virtually abolished it ability to inhibit the inflammatory response elicited by carrageenan, suggesting that the native structure of TSG-6 protein is essential for its anti-inflammatory activity (FIG. 5).

TSG-6 Protein Forms A Stable High Molecular Weight Complex Within the Air Pouch During the Inflammatory Response.

Western blot analysis of air pouch exudates harvested 4 h after injection of air pouches with 20 μg rhuTSG-6 protein simultaneously with carrageenan showed, in addition to the 32 kDa band corresponding to free TSG-6 protein, a second ~120 kDa band recognized by antibody to human TSG-6. The Western blot was developed with a polyclonal rabbit antiserum specific for TSG-6. The 32 kDa band corresponding to free human TSG-6 and the ~120 kDa band were not detected in air pouch exudates from mice injected with carrageenan alone. The ~120 kDa band is of the same size as the complex formed between TSG-6 protein and human IαI (Example I), and it most likely represents a complex between TSG-6 and components of the murine homologue of IαI. The finding that a stable complex similar to the complex of human IαI and TSG-6 is readily formed in the air pouch exudate in compatible with the notion that this complex plays a role in the anti-inflammatory action of TSG-6.

The Inhibitory Effect of TSG-6 Protein on IL-1-elicited Inflammation in the Murine Air Pouch is Comparable to the Effect of Dexamethasone.

Figure 6:
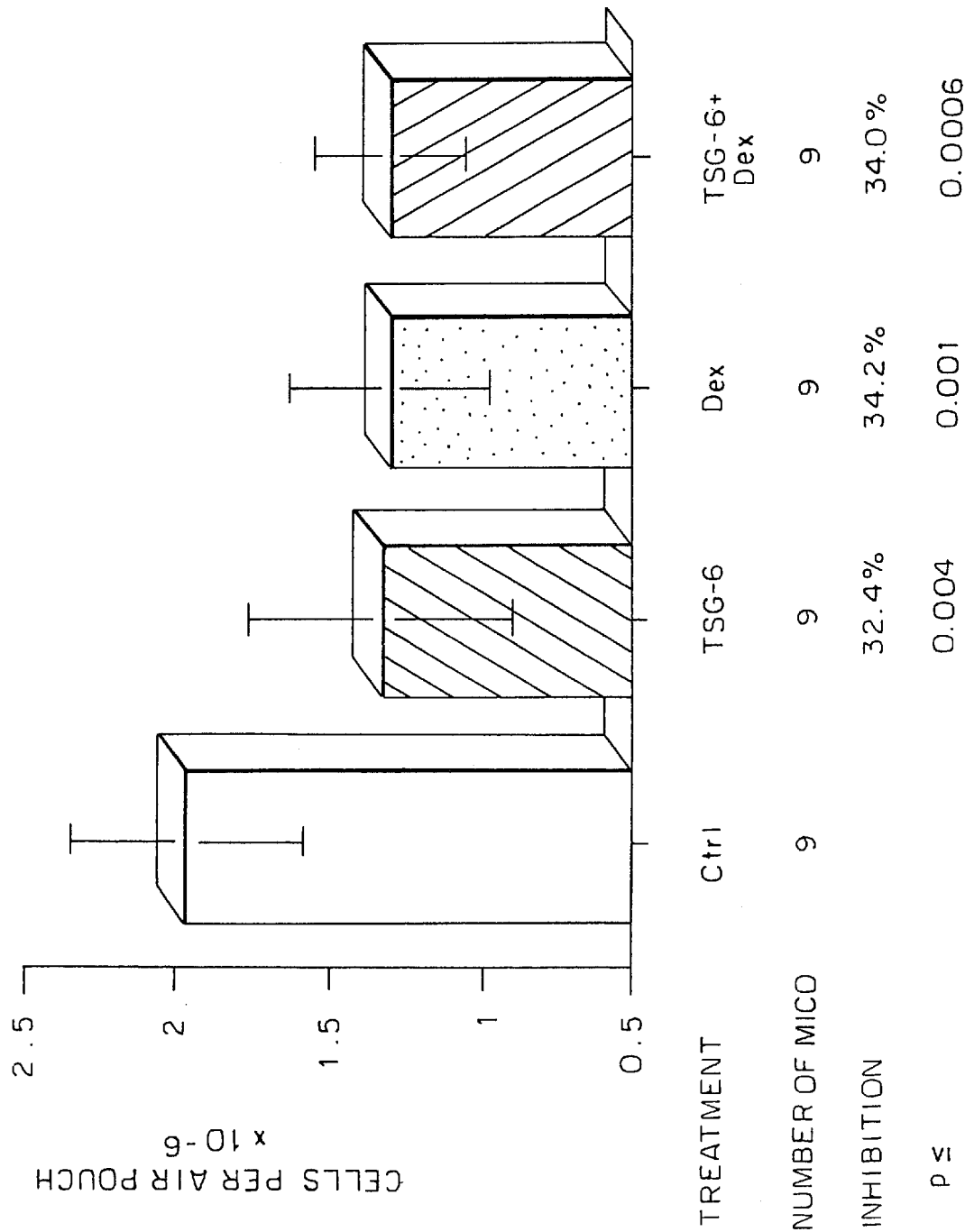
FIG. 6 shows the inhibition of IL-1-elicited cellular infiltration of the murine air pouch by rhuTSG-6 and dexamethasone. Experimental inflammation was induced by the local injection of 40 ng murine IL-1β directly into the air pouch. Dexamethasone was injected i.p. at a dose of 1.5 mg/kg 1 h before the IL-1 administration, whereas rhuTSG-6 protein (20 μg) was injected simultaneously with IL-1 into the air pouch. The number of mice used and the percent inhibition of the cellular infiltration are indicated in the figure. The p-values are based on two-sided t-test.

In order to show that the anti-inflammatory effect of TSG-6 protein is not limited to carrageenan-induced inflammation, murine air pouches were injected with the inflammatory cytokine IL-1β alone or in combination with 20 μg of TSG-6 protein. Administration of TSG-6 protein resulted in a 32.4% inhibition of the inflammatory response, as determined by enumeration of neutrophil infiltration into the air pouch (p≦50.004) (FIG. 6). To determine how the anti-inflammatory action of TSG-6 compares to that of glucocorticoids, another group of mice was injected intraperitoneally with dexamethasone 1 h before IL-1 administration into the air pouch. The dose, timing, and route of administration of dexamethasone were chosen on the basis of earlier studies in which the anti-inflammatory effect of dexamethasone has been optimized. Treatment with dexamethasone resulted in an inhibition of neutrophil infiltration similar in magnitude to that seen with TSG-6. In addition, the effect of the combined treatment with TSG-6 and dexamethasone on IL-1-induced inflammation was also examined. The degree of anti-inflammatory action in this last group was similar to the inhibition seen with TSG-6 or dexamethasone alone, indicating the lack of a cooperative or even additive action of the two agents. These results indicated that the anti-inflammatory action of TSG-6 protein in the murine air pouch model is not limited to carrageenan-induced inflammation as it was also clearly demonstrated in inflammatory lesions elicited by IL-1. In addition, under the conditions employed, the anti-inflammatory action seen after local administration of TSG-6 into the air pouch was of the same magnitude as the inhibitory effect produced by systemic glucocorticoid treatment.

Lack of Inhibition of Plasmin Activity by Mutant Proteins TSG-6$^{K41}$ and TSG-6$^{E48}$.

Figure 7:
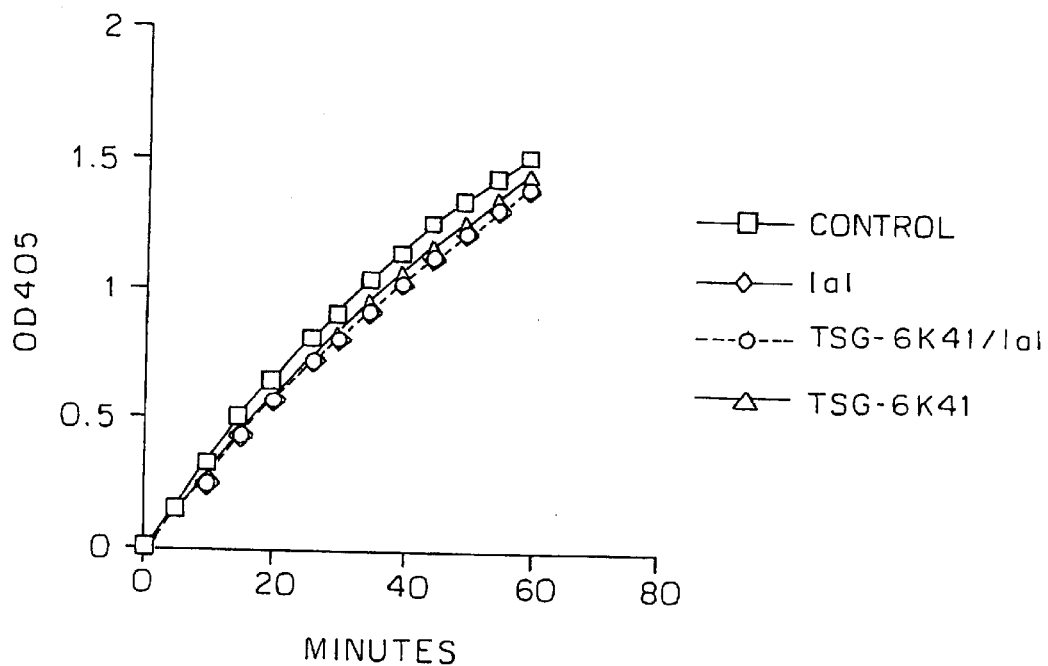
FIG. 7 shows the effect of TSG-$6^{K41}$ protein on the anti-plasmin activity of IαI where plasmin activity is assayed using Chromozym$^R$ PL as a substrate with 3.4 nM plasmin alone (control), in the presence of 18 nM IαI alone (IαI), 167 nM TSG-$6^{E48}$ (TSG-$6^{E48}$) or both 18 nM IαI and 167 nM TSG-$6^{E48}$ (TSG-$6^{E48}$/IαI)
Figure 8:
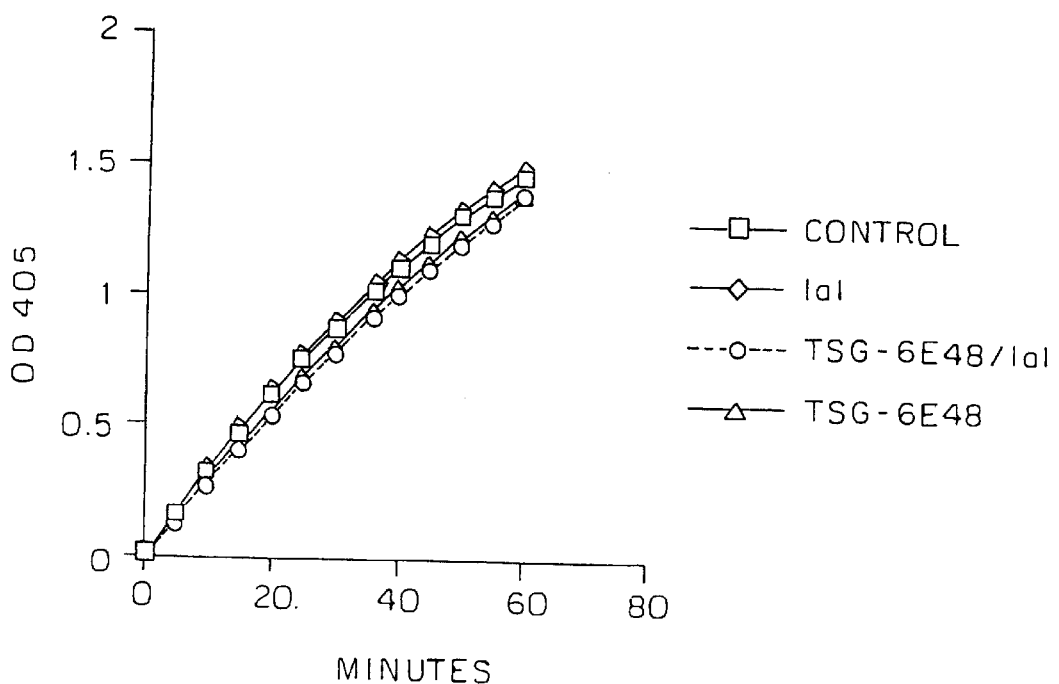
FIG. 8 shows the effect of TSG-$6^{E48}$ on the anti-plasmin activity of IαI where plasmin activity is assayed with 3.4 nM plasmin in the absence of inhibitors (control), in the presence of 18 nM IαI (IαI), 151 nM TSG-$6^{K41}$ (TSG-$6^{K41}$) or both 18 nM IαI and 151 nM TSG-$6^{K41}$ (TSG-$6^{K41}$IαI).
Figure 9:
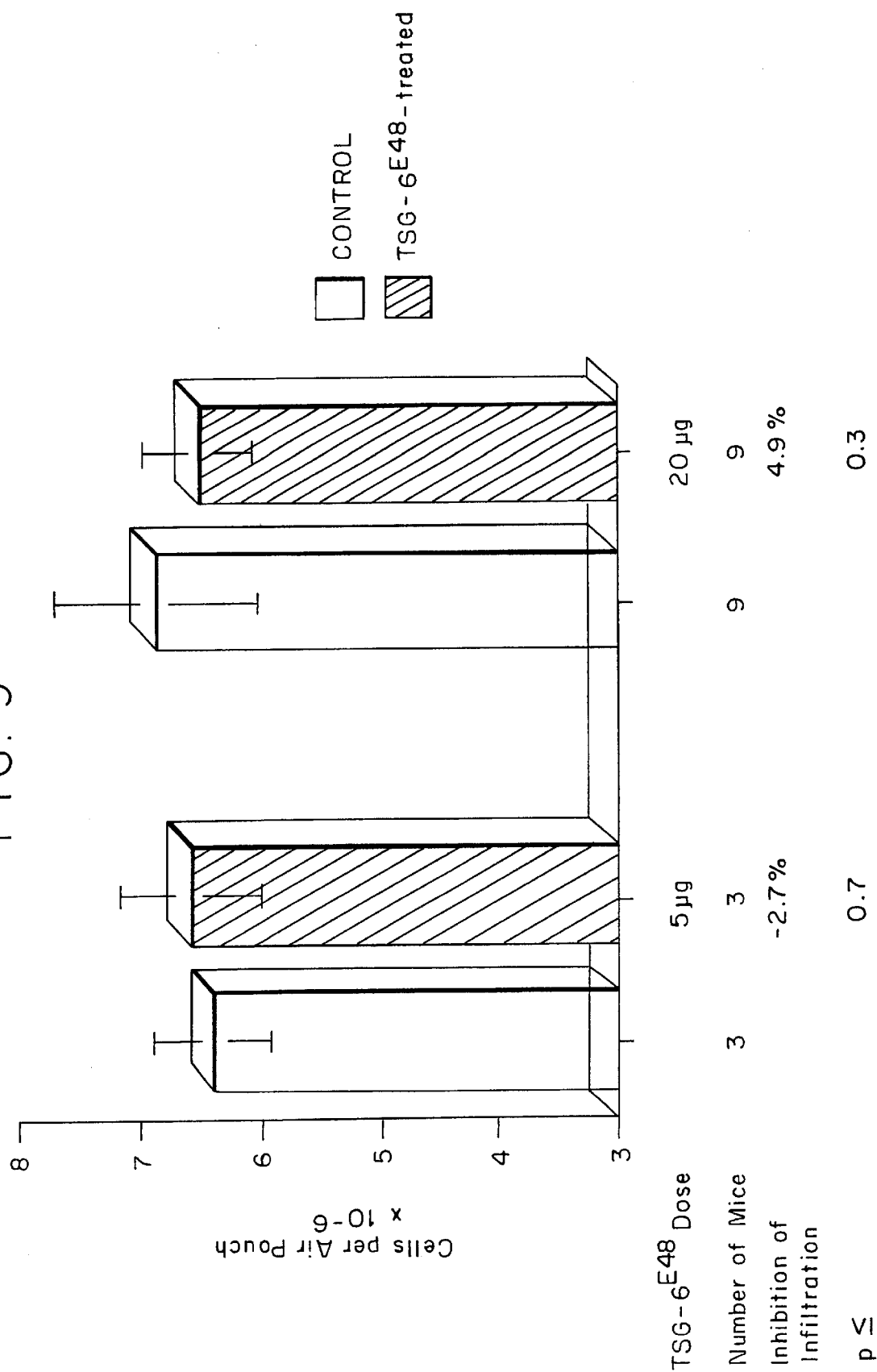
FIG. 9 shows the anti-inflammatory effect of mutant protein TSG-$6^{E48}$. The indicated doses of TSG-$6^{E48}$ protein were injected simultaneously with carrageenan into murine air pouches. The number of mice per group, percent inhibition of cellular infiltration and the p-values are indicated.

Effects of single amino acid exchanges in the N-terminal region on the ability of TSG-6 to form a complex with IαI and to synergize with IαI in the inhibition of plasmin action were examined. Site-directed mutagenesis was employed to introduce selected point mutations into the TSG-6 cDNA. Mutant proteins were produced in insect cell cultures with the aid of the Baculovirus expression system and purified as described in Example I. The mutant proteins readily formed a stable complex with purified human IαI, indistinguishable from the TSG-6/IαI complex formed between wild-type TSG-6 protein and IαI. However, mutant proteins TSG-6$^{K41}$ and TSG-6$^{E48}$, with single amino acid exchanges in an region close to the N-terminus of the mature TSG-6 protein, showed a complete loss of their ability to synergize with IαI in inhibiting the protease activity of plasmin (FIGS. 7 and 8). In the mutant protein TSG-$6^{K41}$, residue $Glu^{41}$ (corresponding to position 24 in the mature protein) is replaced by lysine, and in TSG-$6^{E48}$, $Lys^{48}$ (corresponding to position 31 in the mature protein) is substituted by glutamic acid. The complete loss of the ability TSG-$6^{K41}$ and TSC-$6^{E48}$ to synergize with IαI in the inhibition of plasmin activity suggests that the affected region near the N-terminus of TSG-6 protein is essential for the efficient interaction of TSG-6, IαI and plasmin leading to significant inhibition of plasmin's protease activity.

Anti-inflammatory Activity of the Mutant Proteins TSG-$6^{K41}$ and TSG-$6^{E48}$.

Figure 10:
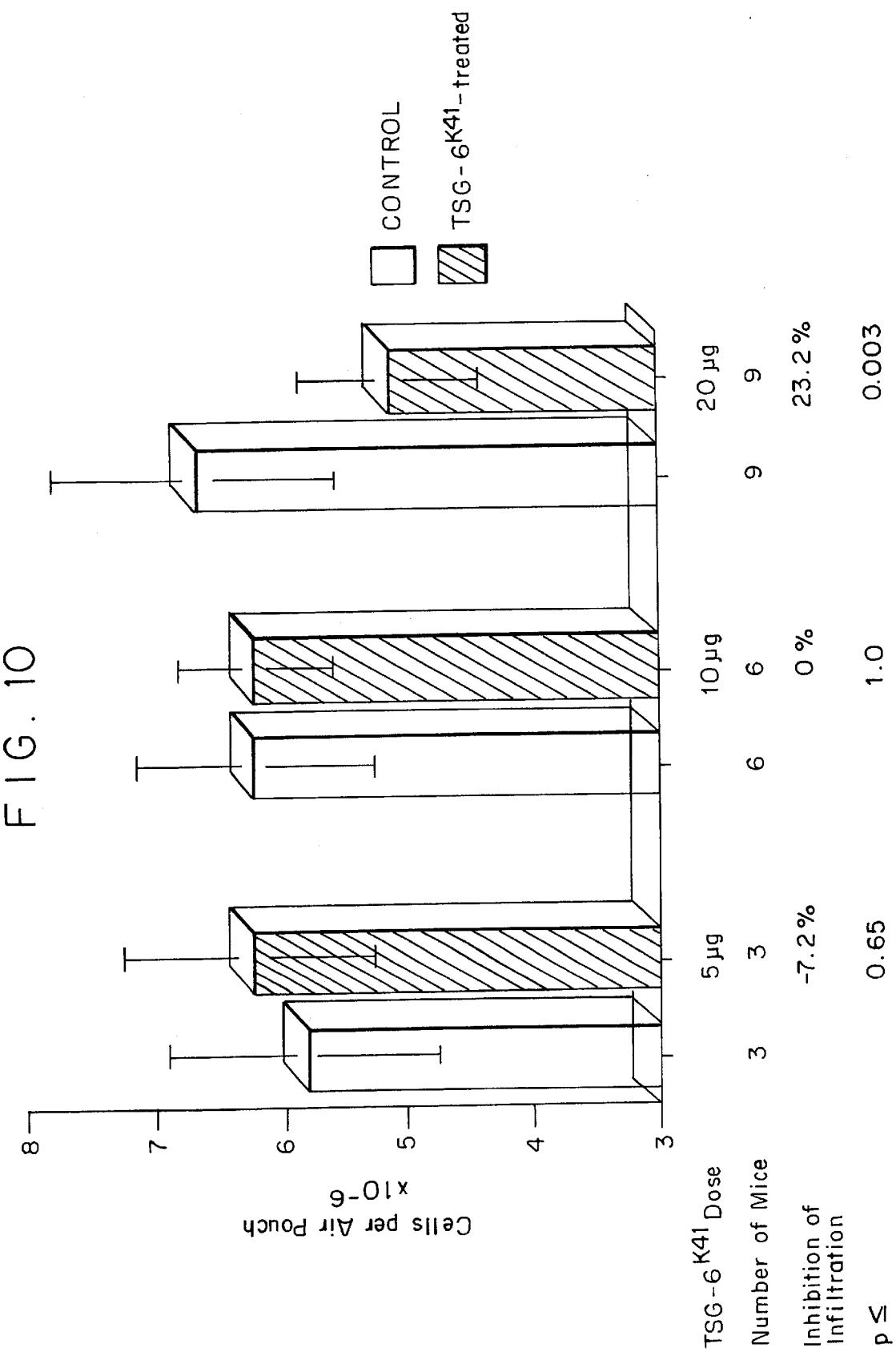
FIG. 10 shows the anti-inflammatory effect of mutant protein TSG-$6^{K41}$. The indicated doses of TSG-$6^{K41}$ were injected simultaneously with carrageenan into murine air pouches. The numbers of mice per group, percent inhibition of cellular infiltration and the p-values are indicated.
Figure 11:
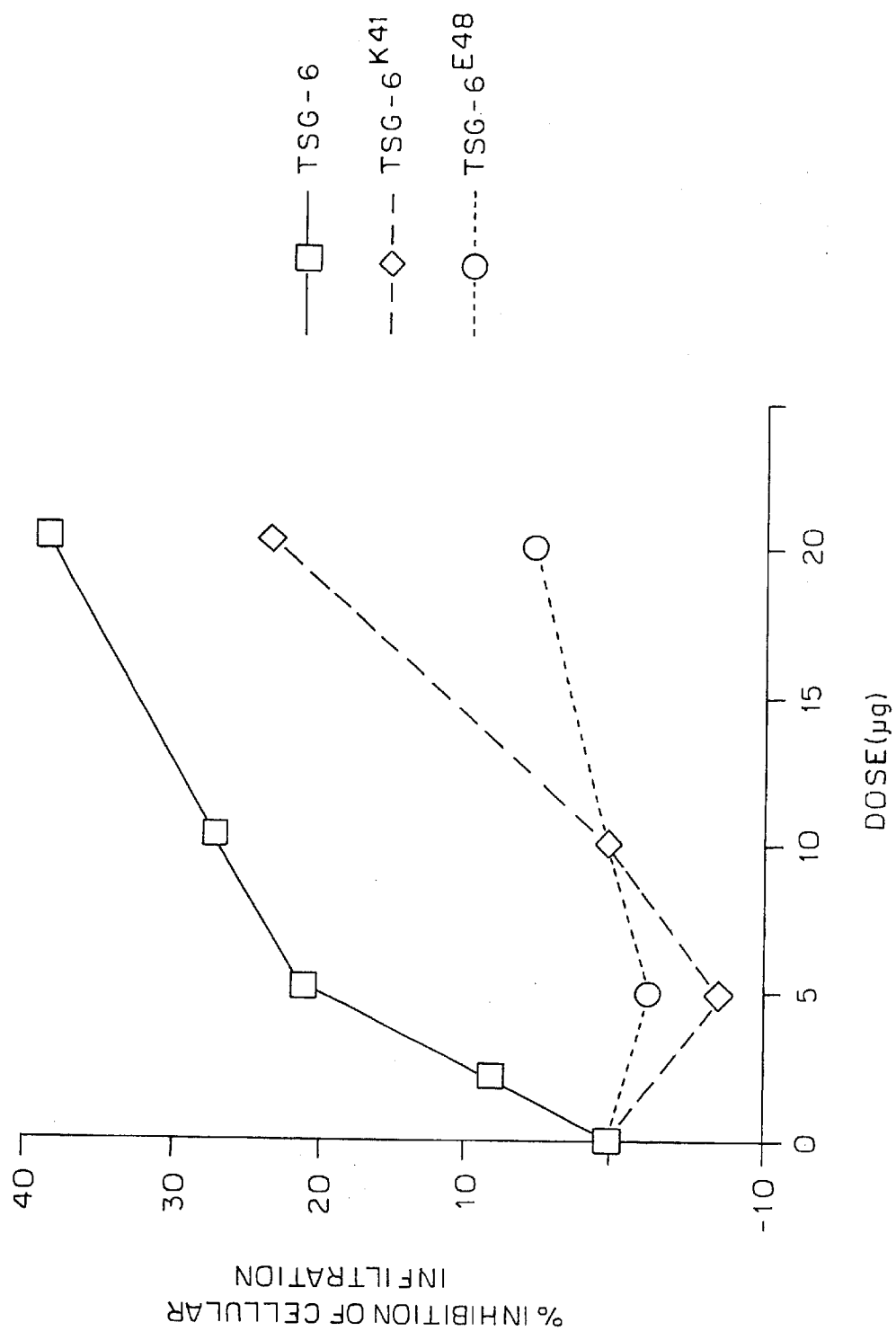
FIG. 11 shows the dose-response curves of the TSG-$6^{K41}$ and TSG-$6^{E48}$ proteins, compared to native rhuTSG-6 (data for native TSG-6 are from FIG. 4).

Single amino acid substitutions in a short sequence close to the N-terminus which resulted in a complete loss of the synergistic inhibitory action of TSG-6 protein and IαI on plasmin activity also showed a dramatic effect on the anti-inflammatory action of those mutant proteins. The substitution of glutamic acid for $Lys^{48}$ resulted in a complete loss of the anti-inflammatory activity (FIG. 9) whereas the substitution of lysine for $Glu^{41}$ resulted in a significantly reduced anti-inflammatory activity detectable only at high TSG-$6^{K41}$ concentrations (FIG. 10). A summary of these finding is presented in FIG. 11.

Discussion

In this example, it is shown that TSG-6 and IαI can indeed cooperatively inhibit the proteinase activity of plasmin. Furthermore, recombinant human TSG-6 protein is shown to exert a potent inhibitory action on carrageenan- or IL-1-elicited acute inflammation in the mouse. These results suggest that induction of TSG-6 by TNF/IL-1 or by LPS represent part of a negative feedback loop operating in the inflammatory response.

Although direct evidence is still lacking, it is likely that the potentiation of the anti-plasmin activity of IαI by TSG-6 is the result of the formation of a stable complex between TSG-6 and components of IαI. Intact IαI is a ~250 kDa molecule composed of three polypeptide chains (heavy chain 1, heavy chain 2 and bikunin) crosslinked to chondroitin sulfate (Enghild et al., supra, 1989; Gebhard et al., supra, 1990). It was shown in Example I that within minutes of mixing IαI with TSG-6 at 37° C., there is an apparent breakdown of the IαI molecule and the ensuing formation of a novel 120 kDa complex stable on SDS-PAGE under reducing conditions. Direct sequencing of the 120 kDA complex showed that it is composed of heavy chain 2, bikunin and TSG-6 (presumably held together by the chondroitin sulfate chain) strongly suggesting that upon interaction of IαI with TSG-6, heavy chain 1 in the IαI molecule is replaced with TSG-6. Since the protease inhibitory action of IαI is mediated solely by the bikunin chain that comprises two Kunitz-type domains (Swaim, 1988; Gebhard et al., supra, 1990), we expected that the novel 120 kDa complex formed between TSG-6 and components of IαI would retain serine protease inhibitory activity. The results in this example show that the addition of recombinant TSG-6 to purified IαI, under conditions described in Example I and shown to lead to the formation of the 120 kDa IαI/TSG-6 complex, resulted in a strong increase in anti-plasmin activity over that of IαI alone (FIG. 1). The observation that a delay in the synergistic anti-plasmin action was seen when IαI and TSG-6 were added directly to the reaction mixtures without preincubation at 37° C. supports the view that formation of the IαI/TSG-6 complex is necessary for potentiation of anti-plasmin action.

To test the hypothesis that through the cooperative inhibitory effect on plasmin TSG-6 and IαI can modulate the protease network during inflammation, the effect of recombinant human TSG-6 protein in the murine air pouch model of acute inflammation was examined. The artificially-induced air pouch becomes lined with cells that resemble the synovial lining of joints, and injection of carrageenan into the air pouch induces a local inflammation that is histo-pathologically similar to synovitis (Edwards et al., *J. Pathol.* 134:147–156, 1981; Sedgwick et al., *Agents & Actions* 11:477–481, 1981). Injection of TSG-6 into the air pouch at the same time as the introduction of an inflammatory stimulus produced a potent anti-inflammatory effect in carrageenan-elicited as well as in IL-1-elicited lesions, as evidenced by a significant reduction in the number of cells infiltrating the air pouch (>95% polymorphonuclear leukocytes) at 4 h after injection of the inflammatory stimulus (FIGS. 3, 4, 5, and 6). The fact that a potent inhibitory effect was seen in this system indicates that TSG-6 affects an early stage in the acute inflammatory response. In view of the rapidity of TSG-6 action, it seems unlikely that TSG-6 acts through the induction of de novo synthesis of other protein mediator(s), consistent with the possibility that a protease cascade-dependent event is affected.

To evaluate its anti-inflammatory action, TSG-6 was injected directly into the air pouch concurrently with the inflammatory stimulus. Evidence was obtained that TSG-6 remains present in the air pouch exudates for at least 4 h after injection. Both 32 kDa and 120 kDa bands containing immunoreactive TSG-6 protein were demonstrated in the exudates. The 120 kDa band is likely to represent a complex of the human TSG-6 protein with components of the murine homologue of IαI. Preliminary observations suggest that systemic (i.p.)administration of TSG-6 can also inhibit carrageenan-elicited neutrophil infiltration into the air pouch.

Further support for a possible connection between the anti-inflammatory effect of TSG-6 and its potentiation of the anti-plasmin activity of IαI comes from our studies with two TSG-6 mutant proteins, TSG-$6^{E48}$ and TSG-$6^{K41}$. These mutant proteins, both of which readily formed a complex with IαI, are indistinguishable from the 120 kDa complex formed by wild-type TSG-6 and IαI. However, both mutant proteins completely failed to enhance the plasmin-inhibitory activity of IαI (FIGS. 7 and 8) suggesting that the N-terminal domain is involved in the interaction among TSG-6, IαI and plasmin, rather than being essential for the interaction between TSG-6 and IαI. The loss of potentiation of the plasmin-inhibitory activity of IαI by TSG-$6^{E48}$ and TSG-$6^{K41}$ correlates with a complete (TSG-$6^{E48}$, FIG. 9) or significant (TSG-$6^{K41}$, FIG. 10) loss of anti-inflammatory activity in the murine air pouch model.

EXAMPLE III

Expression of rhuTSG-6 in Cell Cultures Using the Expression Vector pcDNA3/TSG-6.

The pcDNA3/TSG-6 expression vector was generated by subcloning full-length TSG-6 cDNA into the singular EcoRI restriction site of the mammalian expression vector pcDNA3 (Invitrogen Corp., San Diego, Calif.), thus comprising the complete TSG-6 coding sequence followed by an additional polyadenylation signal. COS cells (African green monkey kidney cells) were grown in DMEM medium containing 10% FCS. For transfection, COS cells were grown in 10 cm Petri dishes to about 50% confluency. Cultures were transfected with 20 μg pcDNA3/TSG-6 plasmid DNA (FIG. 12) by the calcium phosphate precipitation technique with the aid of a transfection kit purchased from 5 Prime-3 Prime, Inc. Transfection was carried out according to the manufacturer's instructions. In short, the plasmid DNA was mixed with the $CaCl_2$ solution and phosphate buffer resulting in the formation of a fine precipitate. This solution was added to the COS cell cultures. After an incubation of 4 h, the cells were subjected to a glycerol shock (15% glycerol in precipitation buffer) for 1 min. The cells were then incubated in DMEM containing 10% FCS for 24 h. After 24 h, the medium was replaced by selection medium of DMEM containing 10% FCS and 500 µg/ml G418. Within five days, most of the cells died and only cells that were resistant to G418 due to stable incorporation of the pcDNA3/TSG-6 plasmid survived. Supernatants of G418-resistant cells were tested for the presence of TSG-6 protein by Western blotting using a monoclonal antibody specific for TSG-6 protein, prepared in our laboratory. The monoclonal mouse antibody to human TSG-6 protein detected two protein bands with molecular weights of 43 kDA and greater than 100 kDa, representing free glycosylated TSG-6 protein and its complexed form, respectively. These two protein bands were not detected in supernatants of untransfected COS cells or COS cells transfected with an unrelated expression vector (pcDNA3/TSG-14).

The references cited in this specification are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for treating rheumatoid arthritis, comprising administering an effective amount of Tumor Necrosis Factor-stimulated gene-6 (TSG-6) protein to a subject in need thereof.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 277 amino acids
      (B) TYPE: amino acid
      (D) TOPOLOGY: linear (ii) MOLECULE TYPE: protein (xi) SEQUENCE DESCRIPTION: SEQ ID NO:1:

```
Met Ile Ile Leu Ile Tyr Leu Phe Leu Leu Leu Trp Glu Asp Thr Gln
 1               5                  10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly His
        50                  55                  60

Leu Ala Thr Tyr Lys Gln Leu Glu Ala Ala Arg Lys Ile Gly Phe His
 65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
                100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Arg
        130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
                180                 185                 190
```

```
Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
        260                 265                 270

Arg Phe Ser His Leu
        275

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ala Val Leu Pro Gln Glu Glu Glu Gly Xaa Gly Gly
1               5                   10

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ser Leu Pro Glu Gly
1               5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Val Leu Pro Gln Glu Glu Glu Gly Ser
1               5                   10

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:
```

```
Ser Leu Pro Gly Glu Ser Glu Glu Met Met
1               5                   10
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Val Xaa Xaa Asp Pro His Phe Ile Ile
1               5
```

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CGGATCCCTG CAGGCCCCGA GTTCGAATCT AGAAGATCTG G                    41
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GCCGGTGTGT ACCACAGAAA AGCACGGTCT GGC                             33
```

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GCACGGTCTG GCAAATACGA GCTCACCTAC GCAGAAGC                        38
```